United States Patent
Radford et al.

(10) Patent No.: US 10,472,521 B2
(45) Date of Patent: Nov. 12, 2019

(54) PHOTOSTABLE FLUORESCENT POLYMERIC TANDEM DYES INCLUDING LUMINESCENT METAL COMPLEXES

(71) Applicant: Becton, Dickinson and Company, Franklin Lakes, NJ (US)

(72) Inventors: Robert J. Radford, Skokie, IL (US); Douglas B. Sherman, Franklin Lakes, NJ (US); Jody Martin, Encinitas, CA (US); James Ghadiali, San Diego, CA (US)

(73) Assignee: BECTON, DICKINSON AND COMPANY, Franklin Lakes, NJ (US)

( * ) Notice: Subject to any disclaimer, the term of this patent is extended or adjusted under 35 U.S.C. 154(b) by 181 days.

(21) Appl. No.: 15/371,064

(22) Filed: Dec. 6, 2016

(65) Prior Publication Data
US 2017/0174892 A1    Jun. 22, 2017

Related U.S. Application Data

(60) Provisional application No. 62/268,264, filed on Dec. 16, 2015.

(51) Int. Cl.
*C09B 69/10*    (2006.01)
*G01N 33/58*    (2006.01)

(52) U.S. Cl.
CPC ......... *C09B 69/109* (2013.01); *G01N 33/582* (2013.01)

(58) Field of Classification Search
CPC ....... C09B 69/109; C09B 57/10; C09B 69/00; C09B 69/102; G01N 33/582; G01N 2458/30; C09K 11/06
See application file for complete search history.

(56) References Cited

U.S. PATENT DOCUMENTS 7,144,950 B2    12/2006    Bazan et al.
7,214,489 B2    5/2007    Bazan et al.
(Continued)

FOREIGN PATENT DOCUMENTS

EP    2315303 A1    8/2009
JP    2010146864    7/2010
(Continued)

OTHER PUBLICATIONS

Traina et al. Design and synthesis of monofunctionalized, water-soluble conjugated polymers for biosensing and imaging applications. J. Am. Chem. Soc. 2011, vol. 133, pp. 12600-12607. (Year: 2011).*

(Continued)

*Primary Examiner* — Shafiqul Haq
(74) *Attorney, Agent, or Firm* — Michael J. Blessent; Bret E. Field; Bozicevic, Field & Francis LLP

(57) ABSTRACT

Photostable polymeric tandem dyes are provided. The photostable polymeric tandem dyes include a water soluble light harvesting multichromophore and a luminescent metal complex covalently linked to the multichromophore and in energy-receiving proximity therewith. Also provided are labelled specific binding members that include the subject dyes. Methods of evaluating a sample for the presence of a target analyte and methods of labelling a target molecule in which the subject polymeric tandem dyes find use are also provided. Systems and kits for practicing the subject methods are also provided.

21 Claims, 5 Drawing Sheets

(56) References Cited

U.S. PATENT DOCUMENTS

| | | | |
|---|---|---|---|
| 7,270,956 | B2 | 9/2007 | Bazan et al. |
| 7,629,448 | B2 | 12/2009 | Bazan et al. |
| 7,666,594 | B2 | 2/2010 | Bazan et al. |
| 7,811,755 | B2 | 10/2010 | Bazan et al. |
| 7,897,684 | B2 | 3/2011 | Bazan et al. |
| 7,914,984 | B2 | 3/2011 | Bazan et al. |
| 8,101,416 | B2 | 1/2012 | Bazan et al. |
| 8,110,673 | B2 | 2/2012 | Bazan et al. |
| 8,158,444 | B2 | 4/2012 | Gaylord et al. |
| 8,227,187 | B2 | 7/2012 | Bazan et al. |
| 8,338,532 | B2 | 12/2012 | Bazan et al. |
| 8,354,239 | B2 | 1/2013 | Gaylord et al. |
| 8,362,193 | B2 | 1/2013 | Gaylord et al. |
| 8,455,613 | B2 | 6/2013 | Gaylord et al. |
| 8,546,081 | B2 | 10/2013 | Bazan et al. |
| 8,575,303 | B2 | 11/2013 | Gaylord et al. |
| 8,617,814 | B2 | 12/2013 | Bazan et al. |
| 8,669,055 | B2 | 3/2014 | Bazan et al. |
| 8,759,444 | B2 | 6/2014 | Bazan et al. |
| 8,802,450 | B2 | 8/2014 | Gaylord et al. |
| 8,835,113 | B2 | 9/2014 | Bazan et al. |
| 8,841,072 | B2 | 9/2014 | Bazan et al. |
| 8,969,509 | B2 | 3/2015 | Liu et al. |
| 8,993,335 | B2 | 3/2015 | Bazan et al. |
| 9,085,799 | B2 | 7/2015 | Bazan et al. |
| 9,139,869 | B2 | 9/2015 | Gaylord et al. |
| 9,159,465 | B2 | 10/2015 | Bazan et al. |
| 9,371,559 | B2 | 6/2016 | Bazan et al. |
| 9,383,353 | B2 | 7/2016 | Gaylord et al. |
| 9,547,008 | B2 | 1/2017 | Gaylord et al. |
| 2008/0197346 | A1 | 8/2008 | Moon et al. |
| 2012/0100628 | A1 | 4/2012 | Sun et al. |
| 2012/0183954 | A1 | 7/2012 | Diwu et al. |
| 2012/0199825 | A1 | 8/2012 | Soga et al. |
| 2014/0350183 | A1 | 11/2014 | Chiu et al. |
| 2015/0226746 | A1 | 8/2015 | Bazan et al. |
| 2016/0266132 | A1 | 9/2016 | Gaylord et al. |
| 2016/0341720 | A1 | 11/2016 | Bazan et al. |
| 2016/0349267 | A1 | 12/2016 | Gaylord et al. |
| 2017/0115298 | A1 | 4/2017 | Gaylord et al. |

FOREIGN PATENT DOCUMENTS

| | | |
|---|---|---|
| KR | 10-1335548 B1 | 12/2013 |
| WO | WO 2004/001379 A2 | 12/2003 |
| WO | WO 2004/077014 A2 | 9/2004 |
| WO | WO 2004/092324 A2 | 10/2004 |
| WO | WO 2005/086617 A2 | 9/2005 |
| WO | WO 2006/074471 A2 | 7/2006 |
| WO | WO 2006/074482 A2 | 7/2006 |
| WO | WO 2006/083932 A2 | 8/2006 |
| WO | WO 2008/100344 A2 | 8/2008 |
| WO | WO 2010/151807 A1 | 12/2010 |
| WO | WO 2011/091086 A1 | 7/2011 |
| WO | WO2011019186 A1 | 7/2011 |
| WO | WO2015165826 A1 | 11/2015 |

OTHER PUBLICATIONS

Qin et al. A water-soluble organometallic conjugated polyelectrolyte for the direct colorimetric detection of silver ion in aqueous media with high selectivity and sensitivity. Macromolecules 2011, vol. 44, pp. 483-489. (Year: 2011).*

Song et al. Synthesis and memory properties of a conjugated copolymer of fluorene and benzoate with chelated europium complex. J. Applied Physics 2006, vol. 100, pp. 1-6. (Year: 2006).*

Xie et al. Polyfluorene-based semiconductors combined with various periodic table elements for organic electronics. Progress in Polymer Science 2012, vol. 37, pp. 1192-1264. (Year: 2012).*

Dinakaran et al. Synthesis and characterization of fluorescent poly[fluorene-co-phenylene-1-(dipyridylamine)] copolymer and its Ru(II) complex. J. Polymer Sci. 2004, vol. 42, pp. 4838-4846. (Year: 2004).*

Thomas et al. Tuthenium and Rhenium complexes of fluorene-based bipyridine ligands: synthesis, spectra, and electrochemistry. Organometallics 2001, vol. 20, pp. 557-563. (Year: 2001).*

Xu et al. A conjugated polymer-Gd(III) complex as pH sensitive contrast agent in magnetic resonance imaging. Front. Chem. China 2010, vol. 5, No. 2, pp. 166-170. (Year: 2010).*

Zhu et al. Water-soluble conjugated polymers for imaging, diagnosis, and therapy. Chem. Rev. 2012, vol. 112, pp. 4687-4735. (Year: 2012).*

Donuru et al., "Near-infrared emissive BODIPY polymeric and copolymeric dyes", Polymer, Oct. 29, 2010, vol. 51, No. 23, pp. 5359-5368.

Hulspas et al. "Flow cytometry and the stability of phycoerythrin-tandem dye conjugates", Cytometry Part A, Nov. 2009, vol. 75A, No. 11, pp. 966-972.

Lee et al. "Recent advances in fluorescent and colorimetric conjugated polymer-based Biosensors", Analyst, 2010, vol. 135, pp. 2179-2189.

Shi et al. "Simple Conjugated Polymers with On-Chain Phosphorescent Iridium(III) Complexes: Toward Ratiometric Chemodosimeters for Detecting Trace Amounts of Mercury(II)", Chem. Eur. J. 2010, vol. 16, pp. 12158-12167.

Wen et al. "Dopamine-Modified Cationic Conjugated Polymer as a New Platform for pH Sensing and Autophagy Imaging", Adv. Funct. Mater. 2013, vol. 23, pp. 764-769.

Wu et al. "A rhodamine-appended water-soluble conjugated polymer: an efficient ratiometric fluorescence sensing platform for intracellular metal-ion probing", Chem. Commun. 2014, vol. 50, pp. 2040-2042.

Zhao et al. "A Quencher-Tether-Ligand Probe and Its Application in Biosensor Based on Conjugated Polymer", Macromolecules, 2008, vol. 41, No. 14, pp. 5373-5378 (Abstract only).

Choi, et al. "Molecular engineering of hybrid sensitizers incorporating an organic antenna into ruthenium complex and their application in solar cells", New J. Chem., 2008,32, 2233-2237.

Mongin, et al. "Two-photon Absorption Engineering of 5-(Fluorenyl)-1,10-phenanthroline-based Ru(II) Complexes", Chimia (Aarau). 2015;69(11):666-9.

Rathore,et al. "Dual-color imaging of cytosolic and mitochondrial zinc ions in live tissues with two-photon fluorescent probes", Org Biomol Chem. Jun. 7, 2014;12(21):3406-12.

Zhang, et al. "Synthesis and Photophysical Properties of π-Conjugated Polymers Incorporated with Phosphorescent Rhenium(I) Chromophores in the Backbones", J. Phys. Chem. B20041083513185-13190.

* cited by examiner

PHOTOSTABLE FLUORESCENT POLYMERIC TANDEM DYES INCLUDING LUMINESCENT METAL COMPLEXES

CROSS-REFERENCE TO RELATED APPLICATIONS

Pursuant to 35 U.S.C. § 119(e), this application claims priority to the filing date of U.S. Provisional Patent Application No. 62/268,264, filed Dec. 16, 2015; the disclosure of which application is herein incorporated by reference.

INTRODUCTION

Fluorescent dyes are compounds which, when irradiated with light of a wavelength which they absorb, emit light of a (usually) different wavelength. Fluorescent dyes find use in a variety of applications in biochemistry, biology and medicine, e.g. in diagnostic kits, in microscopy or in drug screening. Fluorescent dyes are characterized by a number of parameters allowing a user to select a suitable dye depending on the desired purpose. Parameters of interest include the excitation wavelength maximum, the emission wavelength maximum, the Stokes shift, the extinction coefficient, the fluorescence quantum yield and the fluorescence lifetime. Dyes may be selected according to the application of interest in order to, e.g., allow penetration of exciting radiation into biological samples, to minimize background fluorescence and/or to achieve a high signal-to-noise ratio.

Molecular recognition involves the specific binding of two molecules. Molecules which have binding specificity for a target biomolecule find use in a variety of research and diagnostic applications, such as the labelling and separation of analytes, flow cytometry, in situ hybridization, enzyme-linked immunosorbent assays (ELISAs), western blot analysis, magnetic cell separations and chromatography. Target biomolecules may be detected by labelling with a fluorescent dye.

SUMMARY

Photostable polymeric tandem dyes are provided. The photostable polymeric tandem dyes include a water soluble light harvesting multichromophore and a luminescent metal complex covalently linked to the multichromophore and in energy-receiving proximity therewith. Also provided are labelled specific binding members that include the subject dyes. Methods of evaluating a sample for the presence of a target analyte and methods of labelling a target molecule in which the subject polymeric tandem dyes find use are also provided. Systems and kits for practicing the subject methods are also provided.

BRIEF DESCRIPTION OF THE FIGURES

It is understood that the drawings, described below, are for illustration purposes only. The drawings are not intended to limit the scope of the present teachings in any way.

DEFINITIONS

Figure 1:
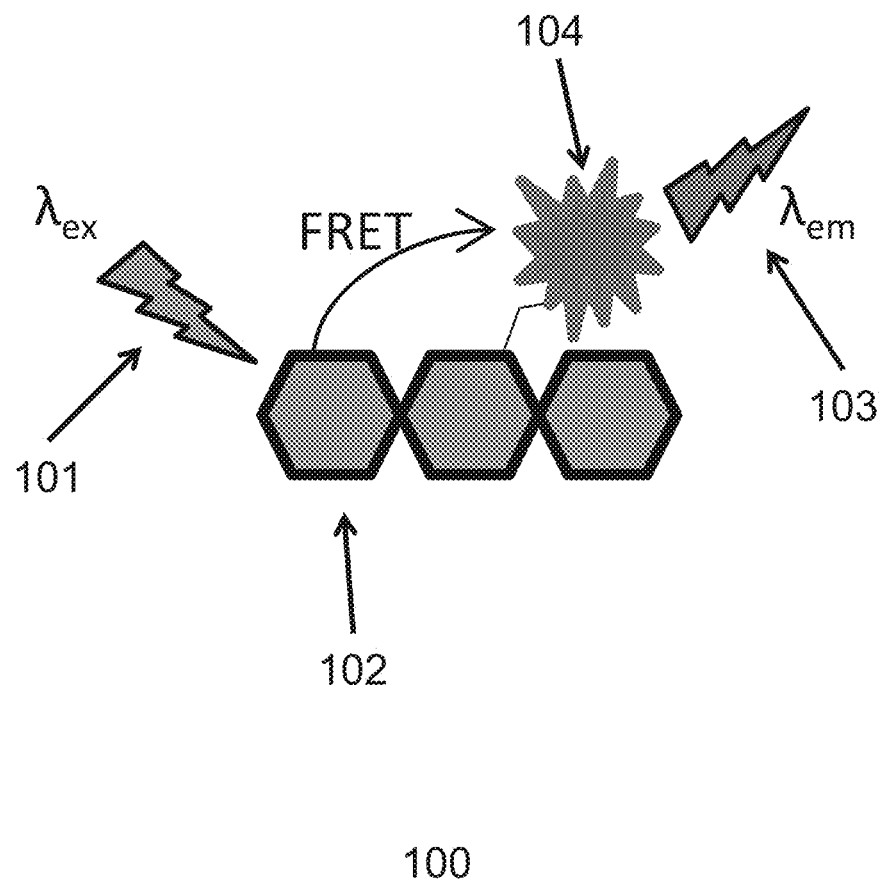
FIG. 1 illustrates a schematic of a photostable polymeric tandem dye (100) that includes a luminescent metal complex as an acceptor. Excitation (101) of the light harvesting multichromophore (102) results in emission (103) from the luminescent metal complex (104) because of Förster Energy Transfer (FRET) from the polymeric light harvesting multichromophore to the metal complex.

Before describing exemplary embodiments in greater detail, the following definitions are set forth to illustrate and define the meaning and scope of the terms used in the description.

Unless defined otherwise, all technical and scientific terms used herein have the same meaning as commonly understood by one of ordinary skill in the art to which this invention belongs. Singleton, et al., DICTIONARY OF MICROBIOLOGY AND MOLECULAR BIOLOGY, 2D ED., John Wiley and Sons, New York (1994), and Hale & Markham, THE HARPER COLLINS DICTIONARY OF BIOLOGY, Harper Perennial, N.Y. (1991) provide one of skill with the general meaning of many of the terms used herein. Still, certain terms are defined below for the sake of clarity and ease of reference.

It must be noted that as used herein and in the appended claims, the singular forms "a", "an", and "the" include plural referents unless the context clearly dictates otherwise. For example, the term "a primer" refers to one or more primers, i.e., a single primer and multiple primers. It is further noted that the claims can be drafted to exclude any optional element. As such, this statement is intended to serve as antecedent basis for use of such exclusive terminology as "solely," "only" and the like in connection with the recitation of claim elements, or use of a "negative" limitation.

As used herein, the term "sample" relates to a material or mixture of materials, in some cases in liquid form, containing one or more analytes of interest. In some embodiments, the term as used in its broadest sense, refers to any plant, animal or bacterial material containing cells or producing cellular metabolites, such as, for example, tissue or fluid isolated from an individual (including without limitation plasma, serum, cerebrospinal fluid, lymph, tears, saliva and tissue sections) or from in vitro cell culture constituents, as well as samples from the environment. The term "sample" may also refer to a "biological sample". As used herein, the term "a biological sample" refers to a whole organism or a subset of its tissues, cells or component parts (e.g. body fluids, including, but not limited to, blood, mucus, lymphatic fluid, synovial fluid, cerebrospinal fluid, saliva, amniotic fluid, amniotic cord blood, urine, vaginal fluid and semen). A "biological sample" can also refer to a homogenate, lysate or extract prepared from a whole organism or a subset of its tissues, cells or component parts, or a fraction or portion thereof, including but not limited to, plasma, serum, spinal fluid, lymph fluid, the external sections of the skin, respiratory, intestinal, and genitourinary tracts, tears, saliva, milk, blood cells, tumors and organs. In certain embodiments, the sample has been removed from an animal or plant. Biological samples may include cells. The term "cells" is used in its conventional sense to refer to the basic structural unit of living organisms, both eukaryotic and prokaryotic, having at least a nucleus and a cell membrane. In certain embodiments, cells include prokaryotic cells, such as from bacteria. In other embodiments, cells include eukaryotic cells, such as cells obtained from biological samples from animals, plants or fungi.

As used herein, the terms "support bound" and "linked to a support" are used interchangeably and refer to a moiety (e.g., a specific binding member) that is linked covalently or non-covalently to a support of interest. Covalent linking may involve the chemical reaction of two compatible functional groups (e.g., two chemoselective functional groups, an electrophile and a nucleophile, etc.) to form a covalent bond between the two moieties of interest (e.g. a support and a specific binding member). In some cases, non-covalent linking may involve specific binding between two moieties of interest (e.g., two affinity moieties such as a hapten and an antibody or a biotin moiety and a streptavidin, etc.). In certain cases, non-covalent linking may involve absorption to a substrate.

As used herein, the term "polypeptide" refers to a polymeric form of amino acids of any length, including peptides that range from 2-50 amino acids in length and polypeptides that are greater than 50 amino acids in length. The terms "polypeptide" and "protein" are used interchangeably herein. The term "polypeptide" includes polymers of coded and non-coded amino acids, chemically or biochemically modified or derivatized amino acids, and polypeptides having modified peptide backbones in which the conventional backbone has been replaced with non-naturally occurring or synthetic backbones. A polypeptide may be of any convenient length, e.g., 2 or more amino acids, such as 4 or more amino acids, 10 or more amino acids, 20 or more amino acids, 50 or more amino acids, 100 or more amino acids, 300 or more amino acids, such as up to 500 or 1000 or more amino acids. "Peptides" may be 2 or more amino acids, such as 4 or more amino acids, 10 or more amino acids, 20 or more amino acids, such as up to 50 amino acids. In some embodiments, peptides are between 5 and 30 amino acids in length.

As used herein the term "isolated," refers to an moiety of interest that is at least 60% free, at least 75% free, at least 90% free, at least 95% free, at least 98% free, and even at least 99% free from other components with which the moiety is associated with prior to purification.

A "plurality" contains at least 2 members. In certain cases, a plurality may have 10 or more, such as 100 or more, 1000 or more, 10,000 or more, 100,000 or more, $10^6$ or more, $10^7$ or more, $10^8$ or more or $10^9$ or more members.

Numeric ranges are inclusive of the numbers defining the range.

As used herein, the term "specific binding" refers to the ability of a capture agent (or a first member of a specific binding pair) to preferentially bind to a particular analyte (or a second member of a specific binding pair) that is present, e.g., in a homogeneous mixture of different analytes. In some instances, a specific binding interaction will discriminate between desirable and undesirable analytes in a sample with a specificity of 10-fold or more for a desirable analyte over an undesirable analytes, such as 100-fold or more, or 1000-fold or more. In some cases, the affinity between a capture agent and analyte when they are specifically bound in a capture agent/analyte complex is at least $10^{-8}$M, at least $10^{-9}$M, such as up to $10^{-10}$M.

As used herein, the terms "affinity" and "avidity" have the same meaning and may be used interchangeably herein. "Affinity" refers to the strength of binding, increased binding affinity being correlated with a lower Kd.

The methods described herein include multiple steps. Each step may be performed after a predetermined amount of time has elapsed between steps, as desired. As such, the time between performing each step may be 1 second or more, 10 seconds or more, 30 seconds or more, 60 seconds or more, 5 minutes or more, 10 minutes or more, 60 minutes or more and including 5 hours or more. In certain embodiments, each subsequent step is performed immediately after completion of the previous step. In other embodiments, a step may be performed after an incubation or waiting time after completion of the previous step, e.g., a few minutes to an overnight waiting time.

As used herein, the terms "evaluating", "determining," "measuring," and "assessing," and "assaying" are used interchangeably and include both quantitative and qualitative determinations.

The term "separating", as used herein, refers to physical separation of two elements (e.g., by size or affinity, etc.) as well as degradation of one element, leaving the other intact.

As used herein, the term "linker" or "linkage" refers to a linking moiety that connects two groups and has a backbone of 100 atoms or less in length. A linker or linkage may be a covalent bond that connects two groups or a chain of between 1 and 100 atoms in length, for example a chain of 1, 2, 3, 4, 5, 6, 8, 10, 12, 14, 16, 18, 20 or more carbon atoms in length, where the linker may be linear, branched, cyclic or a single atom. In some cases, the linker is a branching linker that refers to a linking moiety that connects three or more groups. In certain cases, one, two, three, four or five or more carbon atoms of a linker backbone may be optionally substituted with a sulfur, nitrogen or oxygen heteroatom. The bonds between backbone atoms may be saturated or unsaturated, and in some cases not more than one, two, or three unsaturated bonds are present in a linker backbone. The linker may include one or more substituent groups, for example with an alkyl, aryl or alkenyl group. A linker may include, without limitations, polyethylene glycol; ethers, thioethers, tertiary amines, alkyls, which may be straight or branched, e.g., methyl, ethyl, n-propyl, 1-methylethyl (isopropyl), n-butyl, n-pentyl, 1,1-dimethylethyl (t-butyl), and the like. The linker backbone may include a cyclic group, for example, an aryl, a heterocycle or a cycloalkyl group, where 2 or more atoms, e.g., 2, 3 or 4 atoms, of the cyclic group are included in the backbone. A linker may be cleavable or non-cleavable.

As used herein, the terms "polyethylene oxide", "PEO", "polyethylene glycol" and "PEG" are used interchangeably and refer to a polymeric group including a chain described by the formula —$(CH_2-CH_2-O-)_n$— or a derivative thereof. In some embodiments, "n" is 5000 or less, such as 1000 or less, 500 or less, 200 or less, 100 or less, 50 or less, 40 or less, 30 or less, 20 or less, 15 or less, such as 3 to 15, or 10 to 15. It is understood that the PEG polymeric group may be of any convenient length and may include a variety of terminal groups and/or further substituent groups, including but not limited to, alkyl, aryl, hydroxyl, amino, acyl, acyloxy, and amido terminal and/or substituent groups. PEG groups that may be adapted for use in the subject multichromophores include those PEGs described by S. Zalipsky in "Functionalized poly(ethylene glycol) for preparation of biologically relevant conjugates", Bioconjugate Chemistry 1995, 6 (2), 150-165; and by Zhu et al in "Water-Soluble Conjugated Polymers for Imaging, Diagnosis, and Therapy", Chem. Rev., 2012, 112 (8), pp 4687-4735.

As used herein, the term "alkyl" by itself or as part of another substituent refers to a saturated branched or straight-chain monovalent hydrocarbon radical derived by the removal of one hydrogen atom from a single carbon atom of a parent alkane. Alkyl groups of interest include, but are not limited to, methyl; ethyl, propyls such as propan-1-yl or propan-2-yl; and butyls such as butan-1-yl, butan-2-yl, 2-methyl-propan-1-yl or 2-methyl-propan-2-yl. In some embodiments, an alkyl group includes from 1 to 20 carbon atoms. In some embodiments, an alkyl group includes from 1 to 10 carbon atoms. In certain embodiments, an alkyl group includes from 1 to 6 carbon atoms, such as from 1 to 4 carbon atoms. This term includes, by way of example, linear and branched hydrocarbyl groups such as methyl ($CH_3$—), ethyl ($CH_3CH_2$—), n-propyl ($CH_3CH_2CH_2$—), isopropyl (($CH_3)_2CH$—), n-butyl ($CH_3CH_2CH_2CH_2$—), isobutyl (($CH_3)_2CHCH_2$—), sec-butyl (($CH_3)(CH_3CH_2)CH$—), t-butyl (($CH_3)_3C$—), n-pentyl ($CH_3CH_2CH_2CH_2CH_2$—), and neopentyl (($CH_3)_3CCH_2$—).

The term "substituted alkyl" refers to an alkyl group as defined herein wherein one or more carbon atoms in the alkyl chain have been optionally replaced with a heteroatom such as —O—, —N—, —S—, —S(O)$_n$— (where n is 0 to 2), —NR— (where R is hydrogen or alkyl) and having from 1 to 5 substituents selected from the group consisting of alkoxy, substituted alkoxy, cycloalkyl, substituted cycloalkyl, cycloalkenyl, substituted cycloalkenyl, acyl, acylamino, acyloxy, amino, aminoacyl, aminoacyloxy, oxyaminoacyl, azido, cyano, halogen, hydroxyl, oxo, thioketo, carboxyl, carboxylalkyl, thioaryloxy, thioheteroaryloxy, thioheterocyclooxy, thiol, thioalkoxy, substituted thioalkoxy, aryl, aryloxy, heteroaryl, heteroaryloxy, heterocyclyl, heterocyclooxy, hydroxyamino, alkoxyamino, nitro, —SO-alkyl, —SO-aryl, —SO-heteroaryl, —SO$_2$-alkyl, —SO$_2$-aryl, —SO$_2$-heteroaryl, and —NR$^a$R$^b$, wherein R' and R" may be the same or different and are chosen from hydrogen, optionally substituted alkyl, cycloalkyl, alkenyl, cycloalkenyl, alkynyl, aryl, heteroaryl and heterocyclic.

"Aryl" by itself or as part of another substituent refers to a monovalent aromatic hydrocarbon radical derived by the removal of one hydrogen atom from a single carbon atom of an aromatic ring system. Aryl groups of interest include, but are not limited to, groups derived from aceanthrylene, acenaphthylene, acephenanthrylene, anthracene, azulene, benzene, chrysene, coronene, fluoranthene, fluorene, hexacene, hexaphene, hexalene, as-indacene, s-indacene, indane, indene, naphthalene, octacene, octaphene, octalene, ovalene, penta-2,4-diene, pentacene, pentalene, pentaphene, perylene, phenalene, phenanthrene, picene, pleiadene, pyrene, pyranthrene, rubicene, triphenylene, trinaphthalene and the like. In certain embodiments, an aryl group includes from 6 to 20 carbon atoms. In certain embodiments, an aryl group includes from 6 to 12 carbon atoms. Examples of an aryl group are phenyl and naphthyl.

"Heteroaryl" by itself or as part of another substituent, refers to a monovalent heteroaromatic radical derived by the removal of one hydrogen atom from a single atom of a heteroaromatic ring system. Heteroaryl groups of interest include, but are not limited to, groups derived from acridine, arsindole, carbazole, β-carboline, chromane, chromene, cinnoline, furan, imidazole, indazole, indole, indoline, indolizine, isobenzofuran, isochromene, isoindole, isoindoline, isoquinoline, isothiazole, isoxazole, naphthyridine, oxadiazole, oxazole, perimidine, phenanthridine, phenanthroline, phenazine, phthalazine, pteridine, purine, pyran, pyrazine, pyrazole, pyridazine, pyridine, pyrimidine, pyrrole, pyrrolizine, quinazoline, quinoline, quinolizine, quinoxaline, tetrazole, thiadiazole, thiazole, triazole, benzotriazole, thiophene, triazole, xanthene, benzodioxole and the like. In certain embodiments, the heteroaryl group is from 5-20 membered heteroaryl. In certain embodiments, the heteroaryl group is from 5-10 membered heteroaryl. In certain embodiments, heteroaryl groups are those derived from thiophene, pyrrole, benzothiophene, benzofuran, indole, pyridine, quinoline, imidazole, oxazole and pyrazine.

The term "alkaryl" or "aralkyl" refers to the groups -alkylene-aryl and substituted alkylene-aryl where alkylene, substituted alkylene and aryl are defined herein.

"Alkylene" refers to divalent aliphatic hydrocarbyl groups preferably having from 1 to 6 and more preferably 1 to 3 carbon atoms that are either straight-chained or branched, and which are optionally interrupted with one or more groups selected from —O—, —NR$^{10}$—, —NR$^{10}$C(O)—, —C(O)NR$^{10}$— and the like. This term includes, by way of example, methylene (—CH$_2$—), ethylene (—CH$_2$CH$_2$—), n-propylene (—CH$_2$CH$_2$CH$_2$—), iso-propylene (—CH$_2$CH(CH$_3$)—), (—C(CH$_3$)$_2$CH$_2$CH$_2$—), (—C(CH$_3$)$_2$CH$_2$C(O)—), (—C(CH$_3$)$_2$CH$_2$C(O)NH—), (—CH(CH$_3$)CH$_2$—), and the like. "Substituted alkylene" refers to an alkylene group having from 1 to 3 hydrogens replaced with substituents as described for carbons in the definition of "substituted" below.

"Substituted" refers to a group in which one or more hydrogen atoms are independently replaced with the same or different substituent(s). Substituents of interest include, but are not limited to, alkylenedioxy (such as methylenedioxy), -M, —R$^{60}$, —O$^-$, =O, —OR$^{60}$, —SR$^{60}$, —S$^-$, =S, —NR$^{60}$R$^{61}$, =NR$^{60}$, —CF$_3$, —CN, —OCN, —SCN, —NO, —NO$_2$, =N$_2$, —N$_3$, —S(O)$_2$O$^-$, —S(O)$_2$OH, —S(O)$_2$R$^{60}$, —OS(O)$_2$O$^-$, —OS(O)$_2$R$^{60}$, —P(O)(O$^-$)$_2$, —P(O)(OR$^{60}$)(O$^-$), —OP(O)(OR$^{60}$)(OR$^{61}$), —C(O)R$^{60}$, —C(S)R$^{60}$, —C(O)OR$^{60}$, —C(O)NR$^{60}$R$^{61}$, —C(O)O$^-$, —C(S)OR$^{60}$, —NR$^{62}$C(O)NR$^{60}$R$^{61}$, —NR$^{62}$C(S)NR$^{60}$R$^{61}$, —NR$^{62}$C(NR$^{63}$)NR$^{60}$ R$^{61}$ and —C(NR$^{62}$)NR$^{60}$R$^{61}$ where M is halogen; R$^{60}$, R$^{61}$, R$^{62}$ and R$^{63}$ are independently hydrogen, alkyl, substituted alkyl, alkoxy, substituted alkoxy, cycloalkyl, substituted cycloalkyl, cycloheteroalkyl, substituted cycloheteroalkyl, aryl, substituted aryl, heteroaryl or substituted heteroaryl, or optionally R$^{60}$ and R$^{61}$ together with the nitrogen atom to which they are bonded form a cycloheteroalkyl or substituted cycloheteroalkyl ring; and R$^{64}$ and R$^{65}$ are independently hydrogen, alkyl, substituted alkyl, aryl, cycloalkyl, substituted cycloalkyl, cycloheteroalkyl, substituted cycloheteroalkyl, aryl, substituted aryl, heteroaryl or substituted heteroaryl, or optionally R$^{64}$ and R$^{65}$ together with the nitrogen atom to which they are bonded form a cycloheteroalkyl or substituted cycloheteroalkyl ring. In certain embodiments, substituents include -M, —R$^{60}$, =O, —OR$^{60}$, —SR$^{60}$, —S$^-$, =S, —NR$^{60}$R$^{61}$, =NR$^{60}$, —CF$_3$, —CN, —OCN, —SCN, —NO, —NO$_2$, =N$_2$, —N$_3$, —S(O)$_2$R$^{60}$, —OS(O)$_2$O$^-$, —OS(O)$_2$R$^{60}$, —P(O)(O$^-$)$_2$, —P(O)(OR$^{60}$)(O$^-$), —OP(O) (OR$^{60}$)(OR$^{61}$), —C(O)R$^{60}$, —C(S)R$^{60}$, —C(O)OR$^{60}$, —C(O)NR$^{60}$R$^{61}$, —C(O)O—, —NR$^{62}$C(O) NR$^{60}$R$^{61}$. In certain embodiments, substituents include -M, —R$^{60}$, =O, —OR$^{60}$, —SR$^{60}$, —NR$^{60}$R$^{61}$, —CF$_3$, —CN, —NO$_2$, —S(O)$_2$R$^{60}$, —P(O)(OR$^{60}$)(O$^-$), —OP(O) (OR$^{60}$)(OR$^{61}$), —C(O)R$^{60}$, —C(O)OR$^{60}$, —C(O)NR$^{60}$R$^{61}$, —C(O)O$^-$. In certain embodiments, substituents include -M, —R$^{60}$, =O, —OR$^{60}$, —SR$^{60}$, —NR$^{60}$R$^{61}$, —CF$_3$, —CN, —NO$_2$, —S(O)$_2$R$^{60}$, —OP(O)(OR$^{60}$)(OR$^{61}$), —C(O)R$^{60}$, —C(O)OR$^{60}$, —C(O)O—, where R$^{60}$, R$^{61}$ and R$^{62}$ are as defined above. For example, a substituted group may bear a methylenedioxy substituent or one, two, or three substituents selected from a halogen atom, a (1-4C)alkyl group and a (1-4C)alkoxy group. When the group being substituted is an aryl or heteroaryl group, the substituent(s) (e.g., as described herein) may be referred to as "aryl substituent(s)".

Other definitions of terms may appear throughout the specification.

DETAILED DESCRIPTION

As summarized above, photostable polymeric tandem dyes are provided. The photostable polymeric tandem dyes include a water soluble light harvesting multichromophore and a luminescent metal complex covalently linked to the multichromophore and in energy-receiving proximity therewith. Also provided are labelled specific binding members that include the subject dyes. Methods of evaluating a sample for the presence of a target analyte and methods of labelling a target molecule in which the subject polymeric tandem dyes find use are also provided. Systems and kits for practicing the subject methods are also provided.

Before the various embodiments are described in greater detail, it is to be understood that the teachings of this disclosure are not limited to the particular embodiments described, and as such can, of course, vary. It is also to be understood that the terminology used herein is for the purpose of describing particular embodiments only, and is not intended to be limiting, since the scope of the present teachings will be limited only by the appended claims.

The section headings used herein are for organizational purposes only and are not to be construed as limiting the subject matter described in any way. While the present teachings are described in conjunction with various embodiments, it is not intended that the present teachings be limited to such embodiments. On the contrary, the present teachings encompass various alternatives, modifications, and equivalents, as will be appreciated by those of skill in the art.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present teachings, some exemplary methods and materials are now described.

The citation of any publication is for its disclosure prior to the filing date and should not be construed as an admission that the present claims are not entitled to antedate such publication by virtue of prior invention. Further, the dates of publication provided can be different from the actual publication dates which can be independently confirmed.

As will be apparent to those of skill in the art upon reading this disclosure, each of the individual embodiments described and illustrated herein has discrete components and features which can be readily separated from or combined with the features of any of the other several embodiments without departing from the scope or spirit of the present teachings. Any recited method can be carried out in the order of events recited or in any other order which is logically possible.

All patents and publications, including all sequences disclosed within such patents and publications, referred to herein are expressly incorporated by reference.

In further describing the subject invention, photostable polymeric tandem dyes including donor light harvesting multichromophores and acceptor luminescent metal complexes are described first in greater detail. Next, labelled specific binding members which include the subject photostable polymeric tandem dyes are described. Then, methods of interest in which photostable polymeric tandem dyes find use are reviewed. Systems and kits that may be used in practicing methods of the invention are also described.

Photostable Polymeric Tandem Dyes

As summarized above, the present disclosure provides photostable polymeric tandem dyes. The subject polymeric tandem dyes include a donor water soluble light harvesting multichromophore and a covalently linked luminescent metal complex acceptor in energy-receiving proximity to the multichromophore. The number of luminescent metal complex acceptor units that are linked to the donor water soluble light harvesting multichromophore may vary, where in some instances the number ranges from 1 mol % to 50 mol %, such as from 5 mol % to 25 mol % or from 10 mol % to 25 mol %. In some cases, the luminescent metal complex acceptor is more photostable than an organic fluorophore dye (e.g., a dye that lacks a metal ion such as a xanthene or a cyanine dye). Photodegradation refers to the photochemical modification of a fluorescent molecule leading to a modified molecule with different fluorescence properties (e.g., reduced fluorescence at wavelengths of interest). The water soluble light harvesting multichromophore is itself fluorescent and capable of transferring energy to a linked luminescent metal complex acceptor. As such, excitation of the multichromophore donor leads to energy transfer to and emission from the photostable covalently attached metal complex acceptor.

As used herein, the term "photostable" refers to a fluorescent molecule that is resistant to photodegradation thereby having an emission signal that is substantially stable during exposure to incident excitation light for an extended period of time, e.g., an emission signal that maintains at least 50% intensity for 20 minutes or more (e.g., 40 minutes or more, 50 minutes or more, 60 minutes or more, 90 minutes or more, 2 hours or more, 3 hours or more, 6 hours or more, or even more). In some cases, the exposure of the photostable dye to incident excitation light is continuous. In certain instances, the exposure of the photostable dye to incident excitation light is discontinuous. By "incident excitation light" is meant light having a wavelength and intensity suitable for exciting the light harvesting multichromophore. By "maintains at least X % intensity" is meant that the intensity of the emission signal of the irradiated dye at a given time is at least X % of the emission signal intensity at time zero under the same excitation conditions, where X % can refer to any convenient % intensity from 1 to 100% intensity, e.g., 50% intensity.

In some embodiments, a photostable polymeric tandem dye has an emission signal that maintains at least 60% intensity for 20 minutes or more, such as for 30 minutes or more, 40 minutes or more, 50 minutes or more, 60 minutes or more, 90 minutes or more, 2 hours or more, 3 hours or more, 6 hours or more, or even more. In some instances, a photostable polymeric tandem dye has an emission signal that maintains at least 70% intensity for 20 minutes or more, such as for 30 minutes or more, 40 minutes or more, 50 minutes or more, 60 minutes or more, 90 minutes or more, 2 hours or more, 3 hours or more, 6 hours or more, or even more. In some cases, a photostable polymeric tandem dye has an emission signal that maintains at least 80% intensity for 20 minutes or more, such as for 30 minutes or more, 40 minutes or more, 50 minutes or more, 60 minutes or more, 90 minutes or more, 2 hours or more, 3 hours or more, 6 hours or more, or even more. In certain cases, a photostable polymeric tandem dye has an emission signal that maintains at least 90% intensity for 20 minutes or more, such as for 30 minutes or more, 40 minutes or more, 50 minutes or more, 60 minutes or more, 90 minutes or more, 2 hours or more, 3 hours or more, 6 hours or more, or even more.

Mechanisms for energy transfer from the fluorescent water soluble light harvesting multichromophore donor to the linked luminescent metal complex acceptor include, for example, resonant energy transfer (e.g., Förster (or fluorescence) resonance energy transfer, FRET), quantum charge exchange (Dexter energy transfer) and the like. In some instances, these energy transfer mechanisms are relatively short range; that is, close proximity of the light harvesting multichromophore system to the acceptor metal complex provides for efficient energy transfer. In some instances, under conditions for efficient energy transfer, amplification of the emission from the acceptor metal complex occurs when the number of individual metal complexes in the light harvesting multichromophore system is large; that is, the emission from the luminescent metal complex (e.g., signaling chromophore) is more intense when the incident light (the "pump light") is at a wavelength which is absorbed by the light harvesting multichromophore than when the luminescent metal complex is directly excited by the pump light.

By "efficient" energy transfer is meant 10% or more, such as 20% or more or 30% or more, of the energy harvested by the donor is transferred to the acceptor. By "amplification" is meant that the signal from the acceptor chromophore is 1.5× or greater when excited by energy transfer from the donor light harvesting multichromophore as compared to direct excitation with incident light of an equivalent intensity. The signal may be measured using any convenient method. In some cases, the 1.5× or greater signal refers to an intensity of emitted light. In certain cases, the 1.5× or greater signal refers to an increased signal to noise ratio. In certain embodiments of the polymeric tandem dye, the acceptor chromophore emission is 1.5 fold greater or more when excited by the multichromophore as compared to direct excitation of the acceptor chromophore with incident light.

The linked luminescent metal complex emission of the polymeric tandem dye can have a quantum yield of 0.03 or more, such as a quantum yield of 0.04 or more, 0.05 or more, 0.06 or more, 0.07 or more, 0.08 or more, 0.09 or more, 0.1 or more, 0.15 or more, 0.2 or more, 0.3 or more or even more. In some instances, the polymeric tandem dye has an extinction coefficient of $5 \times 10^5$ cm$^{-1}$M$^{-1}$ or more, such as $6 \times 10^5$ cm$^{-1}$M$^{-1}$ or more, $7 \times 10^5$ cm$^{-1}$M$^{-1}$ or more, $8 \times 10^5$ cm$^{-1}$M$^{-1}$ or more, $9 \times 10^5$ cm$^{-1}$M$^{-1}$ or more, such as $1 \times 10^6$ cm$^{-1}$M$^{-1}$ or more, $1.5 \times 10^6$ cm$^{-1}$M$^{-1}$ or more, $2 \times 10^6$ cm$^{-1}$M$^{-1}$ or more, $2.5 \times 10^6$ cm$^{-1}$M$^{-1}$ or more, $3 \times 10^6$ cm$^{-1}$M$^{-1}$ or more, $4 \times 10^6$ cm$^{-1}$M$^{-1}$ or more, $5 \times 10^6$ cm$^{-1}$M$^{-1}$ or more, $6 \times 10^6$ cm$^{-1}$M$^{-1}$ or more, $7 \times 10^6$ cm$^{-1}$M$^{-1}$ or more, or $8 \times 10^6$ cm$^{-1}$M$^{-1}$ or more. In some embodiments, the polymeric tandem dye has a molar extinction coefficient of $5 \times 10^5$ M$^{-1}$cm$^{-1}$ or more. In certain embodiments, the polymeric tandem dye has a molar extinction coefficient of $1 \times 10^6$ M$^{-1}$cm$^{-1}$ or more.

The subject polymeric tandem dyes provide for photostable fluorescence emissions from luminescent metal complexes that are brighter than the emissions which are possible from such metal complexes in isolation. The linked luminescent metal complex emission of the polymeric tandem dye can have a brightness of 50 mM$^{-1}$cm$^{-1}$ or more, such as 60 mM$^{-1}$cm$^{-1}$ or more, 70 mM$^{-1}$cm$^{-1}$ or more, 80 mM$^{-1}$cm$^{-1}$ or more, 90 mM$^{-1}$cm$^{-1}$ or more, 100 mM$^{-1}$cm$^{-1}$ or more, 150 mM$^{-1}$cm$^{-1}$ or more, 200 mM$^{-1}$cm$^{-1}$ or more, 250 mM$^{-1}$cm$^{-1}$ or more, 300 mM$^{-1}$cm$^{-1}$ or more, or even more. In certain instances, the linked luminescent metal complex emission of the polymeric tandem dye has a brightness that is at least 5-fold greater than the brightness of a directly excited luminescent metal complex, such as at least 10-fold greater, at least 20-fold greater, at least 30-fold greater, at least 50-fold greater, at least 100-fold greater, at least 300-fold greater, or even greater than the brightness of a directly excited luminescent metal complex.

Luminescent Metal Complexes

Aspects of the subject polymeric tandem dyes include a luminescent metal complex that is linked to the water soluble light harvesting multichromophore. By transferring energy of a suitable wavelength from the light harvesting multichromophore to the linked luminescent metal complex the brightness of the luminescent metal complex in the polymeric tandem dye can be can be increased relative to a directly excited metal complex. Any convenient luminescent metal complexes may be utilized in the subject polymeric tandem dyes. In some instances, the linked luminescent metal complex is a luminescent transition metal-ligand complex. Any convenient luminescent transition metal-ligand complexes may be utilized in the subject dyes. Transition metal-ligand complexes can have broad absorption bands in the 300 to 500 nm area of the spectrum due to metal-to-ligand charge transfer transitions (MLCT). The MLCT transitions can also lead to extinction coefficients in the range of 10,000 to 30,000 M$^{-1}$cm$^{-1}$, which is less that the extinction coefficients of organic fluorophores such as xanthene (e.g., fluorescein) or cyanine dyes. The subject polymeric tandem dyes provide for photostable fluorescence emissions from luminescent transition metal-ligand complexes that are brighter than the emissions which are possible from such metal complexes in isolation. Transition metal-ligand complexes can behave as a single chromatophoric unit, in contrast to the lanthanide and actinide complexes.

In certain embodiments, the luminescent transition metal complex includes a 1st row (i.e., with respect to the periodic table of elements) transition metal ion. In some instances, the luminescent transition metal complex is selected from an iron complex, a cobalt complex, a nickel complex, a copper complex and a zinc complex. In certain embodiments, the luminescent transition metal complex includes a 2nd row transition metal ion. In some instances, the luminescent transition metal complex is selected from a ruthenium complex, a rhenium complex, a cadmium complex, a silver complex, and a palladium complex. In certain embodiments, the luminescent transition metal complex includes a 3rd row transition metal ion. In some instances, the luminescent transition metal complex is selected from a rhenium complex, an osmium complex, an iridium complex, a platinum complex, a gold complex, and a mercury complex. In some instances, the linked luminescent metal complex includes a metal ion selected from ruthenium, rhenium, rhodium and osmium.

In certain cases, the linked luminescent metal complex includes a group 13 metal ion. Any convenient group 13 metal ion complexes may be utilized in the subject dyes. In certain embodiments, the linked luminescent metal complex is selected from an aluminum complex, a gallium complex and an indium complex. In some instances, the group 13 metal ion is complexes with a cyclic, aromatic hydroxamic acid-based chelating ligand, e.g., a 1-oxo-2-hydroxy-isoquinoline (1,2-HOIQO) based chelating ligand.

In certain instances, the linked luminescent metal complex is a luminescent lanthanide metal complex. Lanthanide metal ions are themselves fluorescent especially when at a +3 oxidation state, due to their electronic configurations. Energy absorbed by an organic ligand can be transferred to lanthanide (III) excited states to provide for emission bands from the lanthanide metal. Any convenient lanthanide complexes may be utilized in the subject dyes. Lanthanide metal complexes of interest include, but are not limited to, Sm(III), Eu(III), Tb(III) and Dy(III) complexes. In some cases, the linked luminescent metal complex is a luminescent actinide metal complex. Similar to the lanthanides, all but one of the actinides are f-block elements and can have electronic configurations which provide for fluorescence. Actinide metal complexes of interest include, but are not limited to, U(VI), Am(III) and Cm(III) complexes.

Any convenient metal ions of interest may be utilized in the luminescent metal ion complex. Metal ions of interest include, but are not limited to, ruthenium (e.g., Ru(II)), rhenium (e.g., Re(I)), rhodium (e.g., Rh(I), osmium (e.g., Os(II)), iridium (e.g., Ir(III)), zinc (e.g., Zn(II)), nickel (e.g., Ni(II)), cadmium (e.g., Cd(II)), mercury (e.g., Hg(II)), cobalt (e.g., Co(II)), silver (e.g., Ag(I)), gold (e.g., Au(I)), platinum (e.g., Pt(II)), palladium (e.g., Pd (II)), copper (e.g., Cu(I)), aluminum (e.g., Al(III)), gallium (e.g., Ga(III)), indium (e.g., In(III)), samarium (e.g., Sm(III)), europium (e.g., Eu(III)), terbium (e.g., Tb(III)) and dysprosium (e.g., Dy(III)).

Luminescent metal complexes that may be adapted for use as a linked luminescent metal complex in the subject polymeric tandem dyes include, but are not limited to, bis(2,2'-bipyridine)-(5-aminophenanthroline)ruthenium bis (hexafluorophosphate), bis(2,2'-bipyridine)-(5-isothiocyanato-phenanthroline)ruthenium bis(hexafluorophosphate), bis(2,2'-bipyridine)-4'-methyl-4-carboxybipyridine-ruthenium N-succinimidyl ester-bis(hexafluorophosphate), ruthenium-tris(2,2'-bipyridyl) dichloride (Ru(bpy)$_3$), a copper(I) acetylide complex, a rhenium (I) acetylide complex, a copper(I) chalcogenide complex, a silver(I) chalcogenide complex, a gold(I) chalcogenide complex, a europium complex with benzimidazole-substituted pyridine-2-carboxylic acid, a europium complex with benzothiazole- and/or benzoxazole-substituted pyridine-2-carboxylic acids, and a europium(III) β-diketonate complex. It is understood that a variety of counterions may be utilized in the subject linked metal complexes, and that the counterions described herein are optional and interchangeable with any other convenient counterions. It is understood that any convenient ligand of the metal complexes described herein may be selected and adapted for covalent attachment to the multichromophore.

The linked luminescent metal complex may include one or more nitrogen donor ligands. Nitrogen donor ligands that find use in the subject metal complexes include, but are not limited to, pyridines, bipyridines, ter-pyridines, phenanthrolines, bathophenanthrolines, imidazoles, pyrroles, pyrazoles, indazoles, triazoles, pyrazines, pyrinidines, pyridazines, purines, porphyrins, and phthalocyanines. In some cases, the nitrogen containing rings of the ligands may also be further modified, such as by fusion to aromatic rings, for example to yield a benzotriazole or a biquinoline, or by substitution, for example with a heteroaryl substituent or a linker.

Luminescent metal complexes which find use in the subject polymeric tandem dyes can have a particular configuration of coordination sites around the metal ion. In some instances, the complex includes 4, 6 or 8 coordination sites. A variety of geometries find use in the subject metal complexes. In some instances, the configuration is octahedral. The metal complex can include one or more chelating ligands. As used herein, the terms "chelating ligand" and "multidentate ligand" are used interchangeably to refer to a ligand that can coordinate to a metal ion via two or more donor atoms.

In certain instances, the linked luminescent metal complex includes a substituted multidentate metal chelating ligand. In certain instances, the substituted multidentate metal chelating ligand is a multidentate oxygen and/or nitrogen-based ligand. In certain instances, the substituted multidentate metal chelating ligand is a multidentate nitrogen-based ligand, e.g., a ligand that includes multiple N-containing functional groups capable of forming dative bonds to a metal ion. Multidentate nitrogen-based ligands of interest include, but are not limited to, ethylenediamines, tetramethylethylenediamines, pyridines, polypyridyls (including bipyridyls, terpyridyls and others), quinolines, and phenanthrolines. Multidentate oxygen-based ligands of interest include, but are not limited to, benzenedicarboxylates.

It is understood that for any of the polymeric tandem dyes described herein, the metal ions and/or non-covalently bound portions of the ligands of the luminescent metal complex may be bound (e.g., chelated) to the polymer at any convenient time during preparation. For example, a chelating ligand can be covalently linked to a multichromophore of interest to produce a conjugated polymer-ligand precursor having metal ion binding sites at selected sidechain locations along the multichromophore. Metal ions of interest and additional coordinating ligands of interest (e.g., non-covalently bound chelating ligands, e.g., Ru(bpy)$_2$Cl$_2$) may then be subsequently bound to the conjugated polymer-ligand conjugate at any convenient time prior to use (see, e.g., Scheme 1 where a metal ion (M$^{n+}$) and a bipyridine ligand (bpy) can be added to the precursor, e.g., via addition of a reagent such as Ru(bpy)$_2$Cl$_2$)).

Scheme 1: Representation of one embodiment of a method of preparation of a polymeric tandem dye from a conjugated polymer-ligand precursor having a metal ion binding site. In the scheme, L is a linker and the conjugated polymer is represented by three joined hexagons.

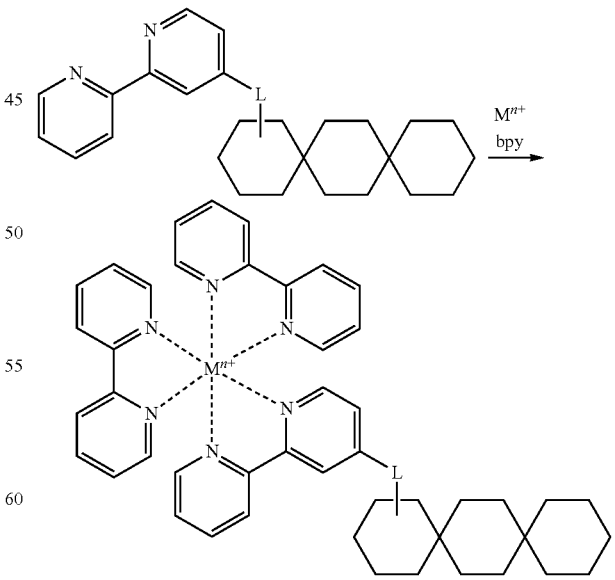

As such, aspects of the present disclosure include conjugated polymer-ligand precursors of any of the subject polymeric tandem dyes described herein. The particular method of preparation of the subject polymeric tandem dyes or precursors thereof is dependent on the ligands and metal complexes selected for covalent attachment to a multichromophore of interest. It is understood that there are many possible variations that may yield equivalent results.

In some embodiments, the linked luminescent metal complex includes a ligand having at least two pyridyl rings, according to the formula (I)

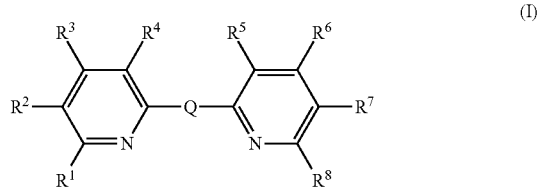

(I)

where the pyridyl rings have the primary ring substituents $R^1$, $R^2$, $R^3$, $R^4$, $R^5$, $R^6$, $R^7$, and $R^8$ that are independently selected from H, halogen, CN, alkyl, substituted alkyl, aryl, heteroaryl, substituted aryl, substituted heteroaryl, perfluoroalkyl, alkoxy (e.g., lower alkoxy having 1-6 carbon atoms), substituted alkoxy, carboxy (—COOH), carboxyalkyl, carboxyalkoxy, carboxyalkylamino, carboxylalkylthio, (e.g., a substituent having 2-7 carbons), amino, salt of amino (e.g., where the counterion is a halide, sulfate, sulfonate, phosphate, perchlorate, tetrafluoroborate, tetraphenylboride or an anion of an aromatic or aliphatic carboxylic acid), sulfonic acid (—SO$_3$H) or a salt of sulfonic acid, alkylamino; dialkylamino and a linker; or optionally $R^5$ and $R^6$ are cyclically linked such that $R^5$, $R^6$ and Q together with the atoms to which them are attached form a 6 membered ring; Q is selected from a covalent bond, a linker, an aryl, a substituted aryl, a heteroaryl, and a substituted hetoaryl; where are least one of $R^1$-$R^8$ and Q is covalently linked to the multichromophore.

In certain instances, a ligand of the metal complex is covalently linked to a sidechain group of the water soluble light harvesting multichromophore. In certain cases of $R^1$, $R^2$, $R^3$, $R^4$, $R^5$, $R^6$, $R^7$, and $R^8$ the alkyl group substituent has 1-6 carbons. In certain instances, the ligand is sulfonated, and includes at least one substituent that is sulfonic acid, or salt of sulfonic acid. In certain instances, the pyridyl rings include at least one aryl or heteroaryl substituent. In some instances, the ligand has no more than two aryl or heteroaryl substituents, which are in some cases attached at $R^1$, $R^3$, $R^6$, and/or $R^8$, in some cases at $R^3$ and $R^6$. In certain embodiments of formula (I), the ligand is a substituted phenanthroline. In certain embodiments of formula (I), Q is a covalent bond and the ligand is a substituted bipyridine.

In some embodiments of formula (I), the ligand has the formula (II)

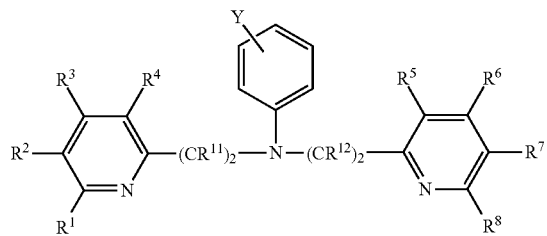

where $R^{11}$ and $R^{12}$ are each independently H, a alkyl (e.g., a lower alky of 1-6 carbons), a substituted alkyl; $R^1$-$R^8$ are as described for formula (I) and Y is one or two optional sulfonic acids or salts of a sulfonic acid.

In some embodiments of formula (I), Q is a 2,6-disubstituted pyridyl, and the ligand is a terpyridyl-based complexing group, according to formula (III):

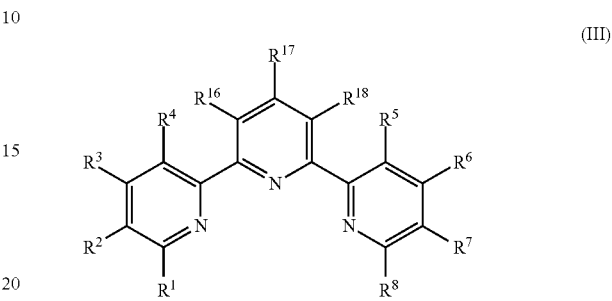

(III)

where $R^1$-$R^4$ and $R^5$-$R^8$ are as defined previously; substituents $R^{16}$, $R^{17}$, and $R^{18}$ are independently H; alkyl, substituted alkyl, perfluoroalkyl, alkoxy (e.g., lower alkoxy having 1-6 carbon atoms), sulfonic acid, salt of sulfonic acid; amino, alkylamino or dialkylamino, where each alkyl group has 1-6 carbons; carboxy; carboxyalkyl, carboxyalkoxy, carboxyalkylamino, or carboxyalkylthio having 2-7 carbons; halogen, or CN. In some cases, one or more of $R^{18}$, $R^{17}$, and $R^{18}$ serves as the attachment point for sulfonic acid or salt of sulfonic acid. In certain cases, $R^{16}$, $R^{17}$, and $R^{18}$ are hydrogen or sulfonic acid. In some instances, $R^{16}$ and $R^{18}$ are hydrogen and $R^{17}$ is sulfonic acid.

Any convenient bipyridine ligands may be covalently attached to the multichromophore in the preparation of the subject dyes. In some cases, the metal complex includes a bipyridine derivative, such as a bipyridine described in U.S. Pat. No. 6,329,205 to Diwu et al; U.S. Pat. No. 6,316,267 to Bhalgat, et al; U.S. Pat. No. 7,087,384 to Autiero, et al. In some embodiments, the polymeric tandem dye includes a substituted multidentate metal chelating ligand (e.g., a bipyridine ligand) described by the formula (IVa):

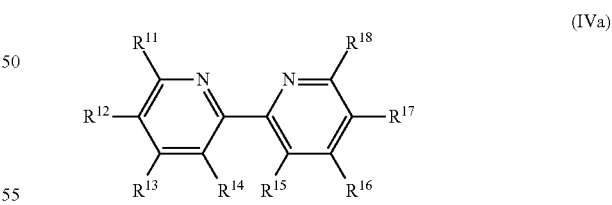

(IVa)

wherein $R^{11}$ to $R^{18}$ are each independently H, an alkyl, a substituted alkyl, a heteroaryl, a substituted heteroaryl, an aryl, a substituted aryl, an alkoxy, a substituted alkoxy, halogen, CN, carboxy, carboxyalkylamino; amino or salt of amino; sulfonic acid (—SO$_3$H) or a salt of sulfonic acid; or a linker, wherein at least one of $R^{11}$ to $R^{18}$ is covalently linked to the multichromophore (e.g., via the linking co-monomer as described herein). In certain instances, the substituted multidentate metal chelating ligand is described by the formula (Va):

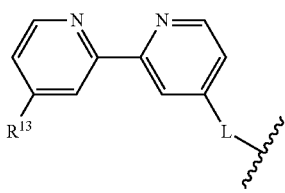

(Va)

wherein R$^{13}$ is H, an alkyl, a substituted alkyl; and L is a linker that is covalently linked to the multichromophore (e.g., via the linking co-monomer as described herein). In certain cases of formula (Va), R$^{13}$ is H. In certain cases of formula (Va), R$^{13}$ is an alkyl (e.g., a lower alkyl having 1-6 carbons). In certain cases of formula (Va), R$^{13}$ is a substituted alkyl (e.g., a substituted lower alkyl having 1-6 carbons).

In some embodiments, the polymeric tandem dye includes a substituted multidentate metal chelating ligand described by the formula (IVb):

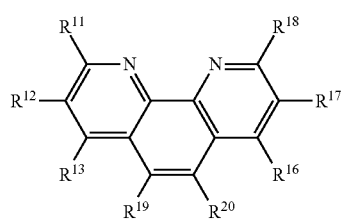

(IVb)

wherein R$^{11}$ to R$^{13}$ and R$^{16}$ to R$^{20}$ are each independently H, an alkyl, a substituted alkyl, a heteroaryl, a substituted heteroaryl, an aryl, a substituted aryl, an alkoxy, a substituted alkoxy, halogen, CN, carboxy, carboxyalkylamino; amino or salt of amino; sulfonic acid (—SO$_3$H) or a salt of sulfonic acid; or a linker, wherein at least one of R$^{11}$ to R$^{18}$ is covalently linked to the multichromophore (e.g., via the linking co-monomer as described herein).

In certain instances, the substituted multidentate metal chelating ligand is described by one of formulae (Vb) and (Vc):

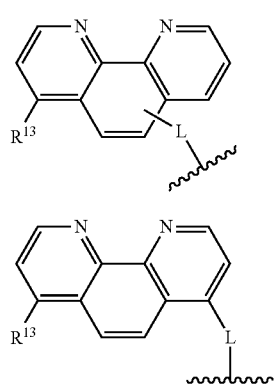

(Vb)

(Vc)

wherein R$^{13}$ is H, an alkyl, a substituted alkyl; and L is a linker that is covalently linked to the multichromophore (e.g., via the linking co-monomer as described herein). In certain cases of formulae (Vb) and (Vc), R$^{13}$ is H. In certain cases of formulae (Vb) and (Vc), R$^{13}$ is an alkyl (e.g., a lower alkyl having 1-6 carbons). In certain cases of formulae (Vb) and (Vc), R$^{13}$ is a substituted alkyl (e.g., a substituted lower alkyl having 1-6 carbons). In certain instances of formulae (IVa-b) and (Va-c), the linker (e.g. L) is covalently linked to a linking co-monomer of the multichromophore via a linking moiety having a backbone of 1-12 carbons and including one or more optional amido (—CONH—) and/or ether (—O—) backbone or linking groups.

In certain embodiments, the ligand of any one of formulae (I) to (V) provides two coordination sites for the metal ion of interest. In certain instances the ligand provides three coordination sites. As such, depending on the nature of the metal ion and the ligands selected, the metal complex can further include additional ligands (e.g., two or more, or three or more additional ligands) that bind to the metal ion. In certain instances, the linked metal complex is of formula (VI):

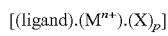

[(ligand).(M$^{n+}$).(X)$_p$]     (VI)

wherein:

each X is any convenient monodentate or multidentate ligand;

p is 2, 3 or 4;

M$^{n+}$ is a metal ion where n is 1, 2 or 3 (e.g., as described herein); and ligand is a linked multidentate ligand that coordinates the metal ion and is covalently linked to the multichromophore. It is understood that the brackets of formula (VI) are used to denote a metal complex which can have an overall charged depending on the charges of M$^{n+}$ and the coordinated ligands, and accordingly, the complex can include any convenient counterions. In certain instances of formula (VI), the linked multidentate ligand is a ligand of any one of formulae (I) to (V).

In some cases of formula (VI), the linked metal complex is of formula (VII):

[(ligand).(M$^{n+}$).(BL)$_2$]     (VII)

where BL is any convenient bidentate ligand (BL), M$^{n+}$ is a metal ion where n is 1, 2 or 3 (e.g., as described herein), and ligand is a linked bidentate ligand of any one of formulae (I) to (V) that is covalently linked to the multichromophore. In certain cases, M$^{n+}$ is selected from ruthenium, osmium, rhenium and rhodium. In certain instances, M$^{n+}$ is Ru$^{2+}$. In certain instances, M$^{n+}$ is Os$^{2+}$. In certain instances, M$^{n+}$ is Re$^+$. In some instances, the linked luminescent metal complex is a substituted tri(bipyridine)ruthenium complex.

In certain embodiments, the linked metal complex is described by formula (VIII):

(VIII)

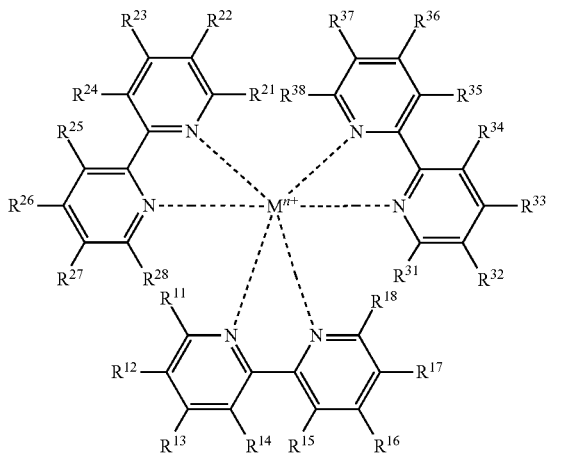

wherein $R^{11}$ to $R^{18}$ are each independently H, an alkyl, a substituted alkyl, a heteroaryl, a substituted heteroaryl, an aryl, a substituted aryl, an alkoxy, a substituted alkoxy, halogen, CN, carboxy, carboxyalkylamino; amino or salt of amino; sulfonic acid (—$SO_3H$) or a salt of sulfonic acid; or a linker; or optionally $R^{14}$ and $R^{15}$ are cyclically linked to form a fused 6 membered ring, wherein at least one of $R^{11}$ to $R^{18}$ is covalently linked to the multichromophore (e.g., via the linking co-monomer as described herein);

$R^{21}$ to $R^{28}$ and $R^{31}$ to $R^{38}$ are each independently H, an alkyl, a substituted alkyl, a heteroaryl, a substituted heteroaryl, an aryl, a substituted aryl, an alkoxy, a substituted alkoxy, halogen, CN, carboxy, carboxyalkylamino; amino or salt of amino; sulfonic acid (—$SO_3H$) or a salt of sulfonic acid; and $M^{n+}$ is a metal ion (e.g., as described herein), wherein in some cases n is 1, 2 or 3. In certain embodiments of formula (VIII), $R^{21}$ to $R^{28}$ and $R^{31}$ to $R^{38}$ are each H. In some embodiments of formulae (VI)-(VIII), the metal ion is selected from ruthenium, osmium, rhenium and rhodium ion. In certain instances of formulae (VI)-(VIII), $M^{n+}$ is $Ru^{2+}$. In certain instances of formulae (VI)-(VIII), $M^{n+}$ is $Os^{2+}$. In certain instances of formulae (VI)-(VIII), $M^{n+}$ is $Re^+$.

In some embodiments of formula (VIII), the metal complex has the formula (IX):

(IX)

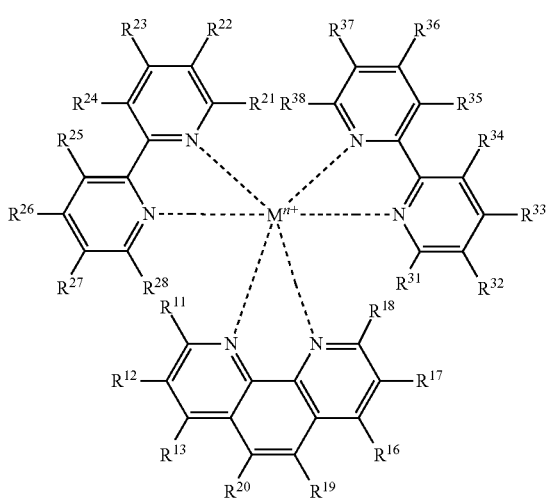

wherein $R^{11}$-$R^{13}$, $R^{16}$-$R^{18}$, $R^{21}$ to $R^{28}$ and $R^{31}$ to $R^{38}$ are as described for formula (VIII) and $R^{19}$ and $R^{20}$ are independently H, an alkyl, a substituted alkyl, a heteroaryl, a substituted heteroaryl, an aryl, a substituted aryl, an alkoxy, a substituted alkoxy, halogen, CN, carboxy, carboxyalkylamino; amino or salt of amino; sulfonic acid (—$SO_3H$) or a salt of sulfonic acid; or a linker; wherein at least one of $R^{11}$ to $R^{13}$ and $R^{16}$ to $R^{20}$ is covalently linked to the multichromophore (e.g., via the linking co-monomer as described herein); $M^{n+}$ is a metal ion (e.g., as described herein), wherein n is 1, 2 or 3.

In certain embodiments of formula (IX), $R^{21}$ to $R^{28}$ and $R^{31}$ to $R^{38}$ are each H. In some embodiments of formula (IX), the metal ion is selected from ruthenium, osmium, rhenium and rhodium. In certain instances of formula (IX), $M^{n+}$ is $Ru^{2+}$. In certain instances of formula (IX), $M^{n+}$ is $Os^{2+}$. In certain instances of formula (IX), $M^{n+}$ is $Re^+$. In some embodiments of formulae (VI)-(IX), the complex is a luminescent ruthenium complex.

Light Harvesting Multichromophores

Aspects of the present disclosure include a light harvesting multichromophore having a conjugated segment comprising a fluorene co-monomer. As used herein, the terms "light harvesting multichromophore", "polymeric dye" and "conjugated polymer" are used interchangeably and refer to a conjugated polymer which has a structure capable of harvesting light with a particular absorption maximum wavelength and converting it to emitted light at a longer emission maximum wavelength. In some cases, the light harvesting multichromophore is itself fluorescent. Conjugated polymers (CPs) are characterized by a delocalized electronic structure and may have an effective conjugation length that is substantially shorter than the length of the polymer chain, because the backbone may contain a large number of conjugated segments in close proximity. In some cases, conjugated polymers are efficient for light harvesting and provide for optical amplification via Forster energy transfer to an acceptor.

As used herein the term "unit" refers to a structural subunit of a polymer. The term unit is meant to include monomers, co-monomers, co-blocks, conjugated segments, repeating units, and the like. A "repeating unit" is a subunit of a polymer that is defined by the minimum number of distinct structural features that are required for the unit to be considered monomeric, such that when the unit is repeated n times, the resulting structure describes the polymer or a block thereof. In some cases, the polymer may include two or more different repeating units, e.g., when the polymer is a multiblock polymer, each block may define a distinct repeating unit. In some cases, a repeating unit of the polymer includes a single monomer group. In certain instances, a repeating unit of the polymer includes two or more monomer groups, i.e., co-monomer groups, such as two, three, four or more co-monomer groups. As used herein, the term "co-monomer" or "co-monomer group" refers to a structural unit of a polymer that may itself be part of a repeating unit of the polymer. In some embodiments, the conjugated polymer includes a block copolymer that is composed of blocks of polymerized monomers. In such cases, the block copolymer may be described as having distinct repeating units each corresponding to a distinct co-block of the polymer. In some cases, the polymer is a diblock copolymer that contains two different co-blocks. In such cases, the polymer may be described as including co-blocks, where each co-block may be composed of co-monomers, such as one, two, three or more co-monomers.

Any convenient light harvesting multichromophores may be adapted to include an absorbance-modifying co-monomer in order to provide a multichromophore having a desirable absorption maximum and a desirable emission maximum for use in transferring energy to a linked metal complex. Light harvesting multichromophores of interest that may be adapted for use in the subject polymeric tandem dyes include, but are not limited to, those multichromophores described by Gaylord et al. in US Publication Nos. 20040142344, 20080293164, 20080064042, 20100136702, 20110256549, 20120028828, 20120252986 and 20130190193 and U.S. Pat. Nos. 8,575,303 and 8,802,450, the disclosures of which Publications and Patents are herein incorporated by reference in their entirety; and Gaylord et al., J. Am. Chem. Soc., 2001, 123 (26), pp 6417-6418; Feng et al., Chem. Soc. Rev., 2010, 39, 2411-2419; and Traina et al., J. Am. Chem. Soc., 2011, 133 (32), pp 12600-12607, the disclosures of which are herein incorporated by reference in their entirety.

In some embodiments, the multichromophores includes a plurality of first optically active units forming a conjugated system, having an absorption wavelength (e.g., as described herein) at which the first optically active units absorb light to form an excited state. In certain instances, the multichromophore includes a conjugated polymer segment or an oligomeric structure including bandgap-lowering n-conjugated repeating units.

The subject polymeric tandem dyes may include a multichromophore that comprises one or more co-monomers selected from a phenylenevinylene co-monomer, a phenyleneethynylene co-monomer, a carbazole co-monomer, a $C_2$-$C_{12}$ alkyne co-monomer, an arylene-ethynylene co-monomer, a heteroarylene-ethynylene co-monomer, an arylene co-monomer and a heteroarylene co-monomer. In some instances, the polymeric tandem dye includes a phenylenevinylene-based multichromophore (e.g., a conjugated polymer including at least 50 mol % of phenylenevinylene co-monomers). In some instances, the polymeric tandem dye includes a phenyleneethynylene-based multichromophore (e.g., a conjugated polymer including at least 50 mol % of phenyleneethynylene co-monomers). In some instances, the polymeric tandem dye includes a carbazole-based multichromophore (e.g., a conjugated polymer including at least 50 mol % of carbazole co-monomers). In some instances, the polymeric tandem dye includes a $C_2$-$C_{12}$ alkyne-based multichromophore (e.g., a conjugated polymer including at least 50 mol % of $C_2$-$C_{12}$ alkyne co-monomers). In some instances, the polymeric tandem dye includes an arylene- or heteroarylene-ethynylene-based multichromophore (e.g., a conjugated polymer including at least 50 mol % of arylene- or heteroarylene-ethynylene co-monomers). In some instances, the polymeric tandem dye includes an arylene- or heteroarylene-based multichromophore (e.g., a conjugated polymer including at least 50 mol % of arylene- or heteroarylene-co-monomers). In certain instances, in addition to the co-monomers described above, the multichromophore includes a linking co-monomer that has a linking group to which may be attached any convenient moieties of interest (e.g., a metal complex or a specific binding member).

In some instances, the polymeric tandem dye is based on a non-fluorene multichromophore (e.g., a conjugated polymer that does not include fluorene co-monomers). It is understood that any of the co-monomers described above (e.g., a phenylenevinylene co-monomer, a phenyleneethynylene co-monomer, a carbazole co-monomer, a $C_2$-$C_{12}$ alkyne co-monomer, an arylene-ethynylene co-monomer, a heteroarylene-ethynylene co-monomer, an arylene co-monomer or a heteroarylene co-monomer) could be utilized in the multichromophore formulae described herein (e.g., formulae (X), (XVII) and (XIX)-(XXIV) in place of a fluorene co-monomer (e.g., F1).

The subject multichromophores may be water soluble. Any convenient water solubilizing groups may be included in the multichromophore to provide for increased water-solubility. While the increase in solubility may vary, in some instances the increase (as compared to the compound without the WSG(s)) is 2 fold or more, e.g., 5 fold, 10 fold, 25 fold, 50 fold, 100 fold or more. The term "water solubilizing group" (WSG) refers to a group that is well solvated in aqueous environments e.g., under physiological conditions, and that imparts improved water solubility upon the molecules to which it is attached. In some embodiments, a WSG increases the solubility of the multichromophore in a predominantly aqueous solution, as compared to a control multichromophore which lacks the WSG. In some instances, the WSGs of the multichromophore are non-ionic side groups capable of imparting solubility in water in excess of 10 mg/mL. The water solubilizing groups may be any convenient hydrophilic group that is well solvated in aqueous environments. In some cases, the hydrophilic water solubilizing group is charged, e.g., positively or negatively charged. In certain cases, the hydrophilic water solubilizing group is a neutral hydrophilic group. In some embodiments, the WSG is a hydrophilic polymer, e.g., a polyethylene glycol, a cellulose, a chitosan, or a derivative thereof. Water solubilizing groups of interest include, but are not limited to, carboxylate, phosphonate, phosphate, sulfonate, sulfate, sulfinate, sulfonium, ester, polyethylene glycols (PEG) and modified PEGs, hydroxyl, amine, ammonium, guanidinium, pyridinium, polyamine and sulfonium, polyalcohols, straight chain or cyclic saccharides, primary, secondary, tertiary, or quaternary amines and polyamines, phosphonate groups, phosphinate groups, ascorbate groups, glycols, including, polyethers, —COOM', —SO$_3$M', —PO$_3$M', —NR$_3^+$, Y', (CH$_2$CH$_2$O)$_p$R and mixtures thereof, where Y' can be any halogen, sulfate, sulfonate, or oxygen containing anion, p can be 1 to 500, each R can be independently H or an alkyl (such as methyl) and M' can be a cationic counterion or hydrogen, —(CH$_2$CH$_2$O)$_{yy}$CH$_2$CH$_2$XR$^{yy}$, —(CH$_2$CH$_2$O)$_{yy}$CH$_2$CH$_2$X—, —X(CH$_2$CH$_2$O)$_{yy}$CH$_2$CH$_2$—, glycol, and polyethylene glycol, wherein yy is selected from 1 to 1000, X is selected from 0, S, and NR$^{ZZ}$, and R$^{ZZ}$ and R$^{YY}$ are independently selected from H and C$_{1-3}$ alkyl. In some cases, a WSG is (CH$_2$)$_x$(OCH$_2$CH$_2$)$_y$OCH$_3$ where each x is independently an integer from 0-20, each y is independently an integer from 0 to 50.

Multiple WSGs may be included at a single location in the subject multichromophores via a branching linker. In certain embodiments, the branching linker is an aralkyl substituent, further di-substituted with water solubilizing groups. As such, in some cases, the branching linker group is a substituent of the multichromophore that connects the multichromophore to two or more water solubilizing groups. In some cases, the incorporation of multiple WSGs via branching linkers imparts a desirable solubility on the multichromophore. In some instances, the WSG is a non-ionic sidechain group capable of imparting solubility in water in excess of 10 mg/m L.

In some embodiments, the multichromophore includes substituent(s) selected from the group consisting of, an alkyl, an aralkyl and a heterocyclic group, each group further substituted with a include water solubilizing groups hydrophilic polymer group, such as a polyethylglycol (PEG) (e.g., a PEG group of 2-20 units).

In certain embodiments, the multichromophore has an absorption maximum wavelength of 500 nm or less, such as a wavelength of 450 nm or less, 440 nm or less, 430 nm or less, 420 nm or less, 410 nm or less, 400 nm or less, or even less. In certain embodiments, the multichromophore absorbs only UV light. In certain instances, the multichromophore has an absorption maximum wavelength in the range of 300 nm to 400 nm. In certain instances, the multichromophore has an absorption maximum wavelength in the range of 400 nm to 450 nm. In some instances, the multichromophore has an emission maximum wavelength in the range of 375 to 900 nm (such as in the range of 380 nm to 900 nm, 390 nm to 900 nm, or 400 nm to 900 nm).

The multichromophore may have any convenient length. In some cases, the particular number of monomeric repeating units or segments of the multichromophore may fall within the range of 2 to 500,000, such as 2 to 100,000, 2 to 30,000, 2 to 10,000, 2 to 3,000 or 2 to 1,000 units or segments, or such as 5 to 100,000, 10 to 100,000, 100 to 100,000, 200 to 100,000, or 500 to 50,000 units or segments. In some instances, the particular number of monomeric repeating units or segments of the multichromophore may fall within the range of 2 to 1,000, such as 2 to 500, 2 to 100, 3 to 100, 4 to 100, 5 to 100, 6 to 100, 7 to 100, 8 to 100, 9 to 100 or 10 to 100 units or segments.

The multichromophore may be of any convenient molecular weight (MW). In some cases, the MW of the multichromophore may be expressed as an average molecular weight. In some instances, the polymeric dye has an average molecular weight in the range of 500 to 500,000, such as from 1,000 to 100,000, from 2,000 to 100,000, from 10,000 to 100,000 or even an average molecular weight in the range of 50,000 to 100,000.

In some embodiments, the absorbance-modifying co-monomer constitutes 5% or more by molarity (e.g., 5 mol %) of the multichromophore, such as 10% or more, 15% or more, 20% or more, 25% or more, 30% or more, 40% or more, 45% or more, 50% or more, 60% or more, 70% or more, or even more by molarity of the multichromophore. In such cases, the multichromophore may include 5 or more repeating units, such as 10 or more, 20 or more, 30 or more, 40 or more, 50 or more, 60 or more, 70 or more, 80 or more, 90 or more, 100 or more, 200 or more, 500 or more, 1000 or more, 10,000 or more, or even more repeating units. In such cases, the multichromophore may include 5 or more co-monomer units, such as 10 or more, 20 or more, 30 or more, 40 or more, 50 or more, 60 or more, 70 or more, 80 or more, 90 or more, 100 or more, 200 or more, 500 or more, 1000 or more, 10,000 or more, or even more co-monomer units. In certain embodiments, the absorbance-modifying co-monomer constitutes 25% or more by molarity of the multichromophore, such as 30% or more, 40% or more, 45% or more, 50% or more, or even more by molarity of the multichromophore, which includes 5 or more repeating units, such as 10 or more, 20 or more, 30 or more, 40 or more, 50 or more, 60 or more, 70 or more, 80 or more, 90 or more, 100 or more repeating units.

The subject multichromophore may have one or more desirable spectroscopic properties, such as a particular absorption maximum wavelength, a particular emission maximum wavelength, extinction coefficient, quantum yield, and the like. In some embodiments, the multichromophore has an emission maximum wavelength in the range of 300 to 900 nm, such as 350 to 850 nm, 350 to 600 nm, 360 to 500 nm, 370 to 500 nm, 380 to 500 nm, 390 to 500 nm or 400 to 500 nm, where specific examples of emission maxima of interest include, but are not limited to: 395 nm±5 nm, 460 nm±5 nm, 490 nm±5 nm, 550 nm±5 nm, 560 nm±5 nm, 605 nm±5 nm, 650 nm±5 nm, 680 nm±5 nm, 700 nm±5 nm, 805 nm±5 nm. In certain instances, the multichromophore has an emission maximum wavelength selected from the group consisting of 395 nm, 460 nm, 490 nm, 550 nm, 560 nm, 605 nm, 650 nm, 680 nm, 700 nm and 805 nm. In certain instances, the multichromophore has an emission maximum wavelength of 395 nm±5 nm.

In some instances, the multichromophore has an extinction coefficient of $5 \times 10^5$ cm$^{-1}$M$^{-1}$ or more, such as $6 \times 10^5$ cm$^{-1}$M$^{-1}$ or more, $7 \times 10^5$ cm$^{-1}$M$^{-1}$ or more, $8 \times 10^5$ cm$^{-1}$M$^{-1}$ or more, $9 \times 10^5$ cm$^{-1}$M$^{-1}$ or more, such as $1 \times 10^6$ cm$^{-1}$M$^{-1}$ or more, $1.5 \times 10^6$ cm$^{-1}$M$^{-1}$ or more, $2 \times 10^6$ cm$^{-1}$M$^{-1}$ or more, $2.5 \times 10^6$ cm$^{-1}$M$^{-1}$ or more, $3 \times 10^6$ cm$^{-1}$M$^{-1}$ or more, $4 \times 10^6$ cm$^{-1}$M$^{-1}$ or more, $5 \times 10^6$ cm$^{-1}$M$^{-1}$ or more, $6 \times 10^6$ cm$^{-1}$M$^{-1}$ or more, $7 \times 10^6$ cm$^{-1}$M$^{-1}$ or more, or $8 \times 10^6$ cm$^{-1}$M$^{-1}$ or more. In such cases, the multichromophore may have 5 or more repeating units, such as 6 or more, 7 or more, 8 or more, 9 or more, 10 or more, or even more repeating units. In some embodiments, the multichromophore has a molar extinction coefficient of $5 \times 10^5$ M$^{-1}$cm$^{-1}$ or more. In certain embodiments, the multichromophore has a molar extinction coefficient of $1 \times 10^6$ M$^{-1}$cm$^{-1}$ or more.

In some instances, the multichromophore has an extinction coefficient of 40,000 cm$^{-1}$M$^{-1}$ per repeating unit or more, such as 45,000 cm$^{-1}$M$^{-1}$ per repeating unit or more, 50,000 cm$^{-1}$M$^{-1}$ per repeating unit or more, 55,000 cm$^{-1}$M$^{-1}$ per repeating unit or more, 60,000 cm$^{-1}$M$^{-1}$ per repeating unit or more, 70,000 cm$^{-1}$M$^{-1}$ per repeating unit or more, 80,000 cm$^{-1}$M$^{-1}$ per repeating unit or more, 90,000 cm$^{-1}$M$^{-1}$ per repeating unit or more, 100,000 cm$^{-1}$M$^{-1}$ per repeating unit or more, or even more. In some instances, the 40,000 cm$^{-1}$M$^{-1}$ per repeating unit or more described herein is an average extinction coefficient. In certain instances, the repeat unit of the multichromophore may include a single monomer, two co-monomers, or three or more co-monomers. In some instances, the multichromophore has an extinction coefficient of 40,000 cm$^{-1}$M$^{-1}$ per co-monomer or more, such as 45,000 cm$^{-1}$M$^{-1}$ per co-monomer or more, 50,000 cm$^{-1}$M$^{-1}$ per co-monomer or more, 55,000 cm$^{-1}$M$^{-1}$ per co-monomer or more, 60,000 cm$^{-1}$M$^{-1}$ per co-monomer or more, 70,000 cm$^{-1}$M$^{-1}$ per co-monomer or more, 80,000 cm$^{-1}$M$^{-1}$ per co-monomer or more, 90,000 cm$^{-1}$M$^{-1}$ per co-monomer or more, 100,000 cm$^{-1}$M$^{-1}$ per co-monomer or more, or even more. In some instances, the 40,000 cm$^{-1}$M$^{-1}$ per co-monomer or more is an average extinction coefficient.

It is understood that in some cases the subject multichromophores may include co-blocks (e.g., n and m co-blocks). The subject multichromophores may include any convenient linear arrangements of n and m co-blocks of various lengths within the structure of the overall polymer. In addition, the multichromophores may include any convenient arrangements of co-monomers within such n and/or m co-blocks. A variety of polymer synthesis methods may be utilized to prepare co-monomers and co-blocks of interest in the preparation of the subject multichromophores. It is understood that in some cases, the polymerization methods may produce a composition including a population of conjugated polymers that includes some variation with respect to the particular length and/or terminal groups (i.e., end groups) present in each conjugated polymer of the population. The formulae depicted herein may refer to a single compound or to a population or sub-population of polymeric compounds.

In some instances, the multichromophore is described by formula (X):

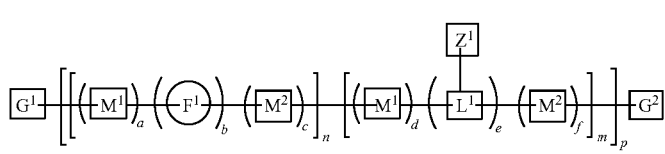

where:
F$^1$ is a fused 6-5-6 tricyclic co-monomer co-monomer;
each M$^1$ and M$^2$ are each independently a co-monomer (e.g., an absorbance-modifying co-monomer);
L$^1$ is a linking co-monomer substituted with a linked luminescent metal complex Z$^1$;
e is 1;
a, b, c, d and f are each independently 0 or 1, wherein a+b+c+d+f≥1;
each n is 0 or an integer from 1 to 100,000;
each m is 0 or an integer from 1 to 10,000;
p is an integer from 1 to 100,000; and
G$^1$ and G$^2$ are each independently selected from the group consisting of a terminal group, a π conjugated segment, a linker and a linked specific binding member. In some instances of formula (X), F$^1$ is a fluorene co-monomer. In some instances of formula (X), F$^1$ is a carbazole co-monomer. In some cases of formula (X), L$^1$ is a fluorene co-monomer. In certain embodiments of formula (X), L$^1$ is a carbazole co-monomer. In some instances of formula (X), L$^1$ is a fluorene co-monomer. In some instances of formula (X), M$^1$ is a fluorene co-monomer. In some cases of formula (X), the linking co-monomer L$^1$ is a fluorene co-monomer. In certain embodiments of formula (X), L$^1$ is an absorbance modifying co-monomer (e.g., as described herein). In certain embodiments of formula (X), M$^1$ is an absorbance modifying co-monomer (e.g., as described herein). In certain embodiments of formula (X), M$^2$ is an absorbance modifying co-monomer (e.g., as described herein).

In some embodiments of formula (X), b is 1. In some instances of formula (X), a is 0. In some cases of formula (X), c is 0. In some instances of formula (X), a is 1. In some cases of formula (X), c is 1. In some instances of formula (X), a+c is ≥1. In certain embodiments of formula (X), d is 0. In certain cases of formula (X), f is 0. In certain embodiments of formula (X), d is 1. In certain cases of formula (X), f is 1. In some instances of formula (X), d+f is ≥1. In some embodiments of formula (X), a+c+d+f=1 (i.e., a is 1, c is 1, d is 1 or f is 1). In some embodiments of formula (X), a+c+d+f=2. In some embodiments of formula (X), a+c+d+f=3. In some embodiments of formula (X), a+c+d+f=4. In certain embodiments of formula (X), e is 1 and d or f is 1, such that d+e+f=2. In certain instances of formula (X), e is 1 and d and f are each 0. In certain instances, e is 1, d+f 1 and m 1. In certain instances, e is 1, d and f are each 0 and m 1. In certain instances, e is 1; d+f=1 and m 1. In some cases, d is 1 and f is 0. In some cases, d is 0 and f is 1. In some embodiments of formula (X), n, m and p are selected such that the multichromophore includes 2 to 100,000 repeat units (i.e., monomeric repeat units) in total, where the multichromophore may include a variety of distinct monomeric repeat units. In some instances, when m is 0, p is 1 and n is 2 to 100,000. In some embodiments of formula (X), L$^1$ is a fluorene co-monomer. It is understood that the conjugated polymer of formula (X) can also be represented by a formula that provides mol % values for each co-monomer in the polymer.

A fused 6-5-6 tricyclic co-monomer is a co-monomer including a tricyclic aromatic group having three fused rings in the configuration 6-5-6, i.e. two benzo ring fused to a central 5 membered ring. The 5-membered ring can be a carbocycle or a heterocycle and can further include a sidechain substituent at the ring atom that is not fused to a benzo ring (i.e., at Y$^1$). In certain instances, the fused 6-5-6 tricyclic co-monomer that finds use in the subject multichromophore is described by the following formula (XI):

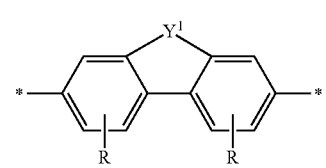

where:
Y$^1$ is —C(R$^1$)$_2$— or —N(R$^1$)—;
each R is independently H or one or more aryl substituents (e.g., as described herein); and
each R$^1$ is independently selected from the group consisting of an alkyl, a substituted alkyl, an aralkyl, a substituted aralkyl, a PEG moiety and -L$^1$-Z$^2$, where L$^1$ is a linker and Z$^2$ is a chemoslective tag (e.g., a tag including a chemoslective functional group), a WSG or a linked metal complex. In some embodiments, when Y$^1$ is —N(R$^1$)—, the fused 6-5-6 tricyclic co-monomer is a carbazole co-monomer. Any convenient carbazole co-monomers may be utilized in the subject multichromophores. In some embodiments, when Y$^1$ is —C(R$^1$)$_2$—, the fused 6-5-6 tricyclic co-monomer is a fluorene co-monomer. Any convenient fluorene co-monomers may be utilized in the subject multichromophores.

A fluorene co-monomer is a co-monomer including an aromatic group having a 9H-fluorene core structure substituted at the 9 position with any convenient sidechain substituent(s). In some cases, the fluorene co-monomer is a 9,9-disubstituted fluorene. The fluorene co-monomer is conjugated to adjacent polymeric backbone groups via any convenient positions of the fluorene core structure, such as any two positions of positions 1-8 (see numbering scheme below). In some embodiments, the fluorene core structure is linked to adjacent groups of the polymer backbone via the 2 and 7 positions. In certain embodiments, the fluorene co-monomer is described by the following formula (XII):

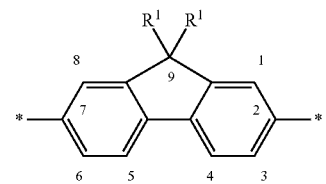

where: each $R^1$ is independently selected from the group consisting of an alkyl, a substituted alkyl, an aralkyl, a substituted aralkyl, a PEG moiety and -$L^2$-$Z^2$, where $L^2$ is a linker and $Z^2$ is a chemoslective tag (e.g., a tag including a chemoslective functional group), a WSG or a linked metal complex. In some cases, $Z^2$ is a chemoslective tag that finds use in covalently linking the multichromophore to an acceptor metal complex (e.g., as described herein). In certain embodiments, $L^2$ is a branched linker (e.g., a substituted benzyl group) that links to two or more $Z^2$ groups (e.g., WSGs such as PEG groups of 2-20 polyethylene glycol units). As used in the formula herein, * denotes a site for covalent attachment to unsaturated backbone of a conjugated polymer or a terminal group.

In certain instances, the fluorene co-monomer is described by the formula (XIII):

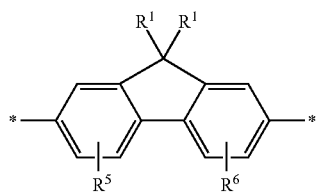

(XIII)

where: each $R^1$ is as defined above; and $R^5$ and $R^6$ are independently selected from the group consisting of H, a water solubilizing group (WSG), or an aryl substituent (e.g., as described herein).

In some instances, the fluorene co-monomer is described by the formula (XIV):

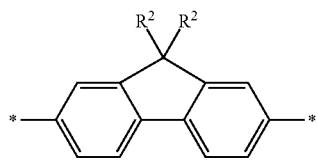

(XIV)

where each $R^2$ is a alkyl substituted with a water solubilizing group or a branched linker connected to two or more water solubilizing groups (e.g., a PEG-disubstituted benzyl or a PEG substituted alkyl). In certain embodiments, the fluorene co-monomer is described by the following formula (XV):

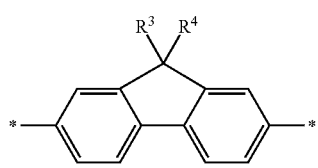

(XV)

where $R^3$ is an alkyl or an aralkyl substituted with a water solubilizing group (e.g., a PEG substituted alkyl or aralkyl), and $R^4$ is $L^2$-$Z^2$ wherein $L^2$ is a linker and $Z^2$ is a chemoselective tag or a linked metal complex. In some instances, fluorene co-monomer is described by the formula (XVI):

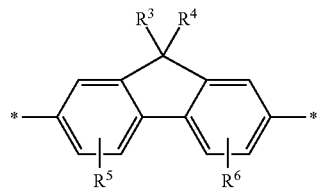

(XVI)

wherein:
$R^3$ is a substituent comprising a water solubilizing group;
$R^4$ is $L^2$-$Z^2$ wherein $L^2$ is a linker and $Z^2$ is a chemoselective tag (e.g., for conjugation to an acceptor metal complex); and
$R^5$ and $R^6$ are independently selected from the group consisting of H, a water solubilizing group and an aryl substituent (e.g., an alkyl, a substituted alkyl, an alkoxy, a substituted alkoxy, a halogen or a nitro).

In some embodiments of formula (X), a, c, d and f are each 0 and b and e are each 1. In certain embodiments of formula (X), $F^1$ is a fluorene co-monomer of formula (XIV) as described herein, where each $R^2$ is independently an alkyl substituted with a water solubilizing group, such as each $R^2$ is —$(CH_2)x(OCH_2CH_2)yOCH_3$ where each x is independently 0 or an integer from 1-20, each y is independently 0 or an integer from 1 to 50. In certain embodiments of formula (X), $L^1$ is a fluorene co-monomer of formula (XV) as described herein. In some embodiments of formula (X), at least one of $G^1$ and $G^2$ is a substituted aryl group, e.g., an aryl group substituted with a linker (e.g., a C1-C6 alkyl linker) terminated with a carboxylic acid functional group.

In some instances of formula (X):
a, c, d and f are each 0 and b and e are each 1;
$F^1$ is a fluorene co-monomer of formula (XIV) where each $R^2$ is independently an alkyl substituted with a water solubilizing group, such as each $R^2$ is —$(CH_2)x(OCH_2CH_2)yOCH_3$ where each x is independently 0 or an integer from 1-20, each y is independently 0 or an integer from 1 to 50;
$L^1$ is a fluorene co-monomer of formula (XV) where $R^3$ is an alkyl or an aralkyl substituted with a water solubilizing group (e.g., a PEG substituted alkyl or aralkyl), and $R^4$ is $L^2$-$Z^2$ wherein $L^2$ is a linker and $Z^2$ is a chemoselective tag (e.g., an amino group, —$NH_2$) or a linked metal complex;
at least one of $G^1$ and $G^2$ is a substituted aryl group, e.g., an aryl group substituted with a linker (e.g., a C1-C6 alkyl linker) terminated with a carboxylic acid functional group or a linked specific binding member (e.g., as described herein).

In some cases, the multichromophores include, as part of the polymeric backbone, the following formula (XVII):

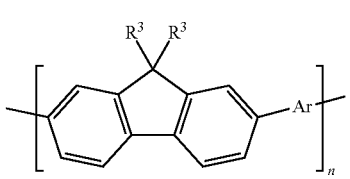

(XVII)

where each $R^3$ is independently a water solubilizing group connected via an optional linker, or an optionally substituted alkyl, aralkyl or aryl group; Ar is an optionally substituted aryl or heteroaryl group; and n is an integer from 1 to 100,000. In certain embodiments, each $R^3$ is independently a substituted alkyl group. In certain embodiments, each $R^3$ is independently a substituted aralkyl group. In some cases, each $R^3$ and each Ar are independently substituted (via an optional linker) with a water solubilizing group, an acceptor chromophore (e.g., linked metal complex), a chemoselective functional group or a specific binding moiety.

In some embodiments of formulae (XI)-(XVII), one or more of $R^1$, $R^2$, $R^3$ and/or $R^4$ is independently selected from $(CH_2)_x(OCH_2CH_2)_yOCH_3$ where each x is independently an integer from 0-20, each y is independently an integer from 0 to 50; and a benzyl optionally substituted with one or more halogen, hydroxyl, $C_1$-$C_{12}$ alkoxy, or $(OCH_2CH_2)_zOCH_3$ where each z is independently an integer from 0 to 50. In some instances, each one or more of $R^1$, $R^2$, $R^3$ and/or $R^4$ is $(CH_2)_3(OCH_2CH_2)_{11}OCH_3$. In some embodiments of formulae (XI)-(XVII), one or more of $R^1$, $R^2$, $R^3$ and/or $R^4$ is a benzyl substituted with at least one WSG groups (e.g., one or two WSG groups) selected from $(CH_2)_x(OCH_2CH_2)_yOCH_3$ where each x is independently an integer from 0-20 and each y is independently an integer from 0 to 50.

As used herein, the terms "chemoselective functional group" and "chemoselective tag" are used interchangeably and refer to a functional group that can selectively react with another compatible functional group to form a covalent bond, in some cases, after optional activation of one of the functional groups. Chemoselective functional groups of interest include, but are not limited to, thiols and maleimide or iodoacetamide, amines and carboxylic acids or active esters thereof, as well as groups that can react with one another via Click chemistry, e.g., azide and alkyne groups (e.g., cyclooctyne groups), as well as hydroxyl, hydrazido, hydrazino, aldehyde, ketone, azido, alkyne, phosphine, epoxide, and the like.

Any convenient linking co-monomers ($L^1$) may be incorporated into the subject multichromophores to provide for a linking group to which may be attached any convenient moieties of interest (e.g., a lined metal complex). Linking co-monomers of interest include, but are not limited to, a fluorene co-monomer (e.g., as described herein), a phenylenevinylene co-monomer, a phenyleneethynylene co-monomer, a carbazole co-monomer, a $C_2$-$C_{12}$ alkyne co-monomer, an arylene-ethynylene co-monomer, a heteroarylene-ethynylene co-monomer, an arylene co-monomer and a heteroarylene co-monomer.

Any convenient chemoselective functional groups may be included in the subject multichromophores (e.g., at the —$Z^2$ and/or in the $G^1$ or $G^2$ terminal groups, including, but are not limited to, carboxylic acid, active ester (e.g., NHS or sulfo-NHS ester), amino, hydroxyl, thiol, maleimide, iodoacetyl, hydrazido, hydrazino, aldehyde, ketone, azido, alkyne, phosphine and epoxide. It is understood that in the polymeric tandem dye structures described herein, in some cases, the groups $Z^1$ and $Z^2$ appear at a equivalent position in the structure where these groups can be used interchangeably to refer to either a linked metal complex or a chemoselective functional group that is capable of subsequent conjugation to a metal complex to produce the linked metal complex.

In certain cases, the linking co-monomer is a substituted aryl co-monomer. In certain cases, the linking co-monomer is a substituted heteroaryl co-monomer. In certain cases, the linking co-monomer is a substituted or unsubstituted 1,4-phenyl, a substituted or unsubstituted 1,3-phenyl, a substituted or unsubstituted 4,4'-biphenyl, a substituted or unsubstituted 2,5-pyridyl, and a substituted or unsubstituted 2,6-pyridyl. In some instances, the linking co-monomer is a fluorene co-monomer. In certain instances, the linking co-monomer is an absorbance-modifying co-monomer (e.g., as described herein).

Any convenient end groups (e.g., $G^1$ and $G^2$) may be utilized at the terminals of the subject multichromophores. As used herein, the terms "end group" and "terminal group" are used interchangeably to refer to the groups located at the terminals of the polymeric structure of the multichromophore, e.g., as described herein. $G^1$ and $G^2$ groups of interest include, but are not limited to a terminal capping group, a π conjugated segment, a linker and a linked specific binding member. In some embodiments, a terminal capping groups is a monovalent group which is conjugated to the backbone of the multichromophore after polymerization. In certain instances, the terminal capping group is an aryl, a substituted aryl, a heteroaryl, a substituted heteroaryl, an alkyl or a substituted alkyl. In certain cases, the terminal capping group is derived from a monomer used in the method of polymerization, e.g., a terminal group such as a halogen (e.g., Br), a boronic acid or a boronic ester, which is capable of undergoing further conjugation. In some instances, $G^1$ and/or $G^2$ is a π conjugated segment. As used herein, a π conjugated segment refers to any convenient segment of a conjugated polymer to which the multichromophore may be conjugated, i.e., allowing delocalization of pi electron across adjacent units. In certain embodiments, $G^1$ and/or $G^2$ is a linker, such as a linker including a functional group suitable for conjugation to a specific binding moiety. It is understood that linkers located at the $G^1$ and/or $G^2$ positions of the multichromophore may be selected so as to be orthogonal to any other linkers including chemoselective tags that may be present at a sidechain of the multichromophore (e.g., at $Z^2$). In certain embodiments, an amino functional group or derivative thereof is included at $G^1$ and/or $G^2$ and a carboxylic acid functional group or derivative thereof is included at $Z^2$. In certain embodiments, a carboxylic acid functional group or derivative thereof is included at $G^1$ and/or $G^2$ and an amino functional group or derivative thereof is included at $Z^2$.

In some embodiments, the absorbance-modifying co-monomer is an optionally substituted aryl or heteroaryl co-monomer. Any convenient aryl or heteroaryl co-monomers may be utilized in the subject multichromophores as absorbance-modifying co-monomers. The absorbance-modifying co-monomer or band gap modifying unit may be evenly or randomly distributed along the conjugated polymer. In certain embodiments, the absorbance-modifying co-monomer is an optionally substituted co-monomer selected from 2,1,3-benzothiadiazole, 2,1,3-benzoxadiazole, benzoxidazole, benzoselenadiazole, benzotellurodiazole, naphthoselenadiazole, 4,7-di(thien-2-yl)-2,1,3-benzothiadiazole, squaraine dyes, quinoxalines, perylene, perylene diimides, diketopyrrolopyrrole, thienopyrazine low bandgap commercial dyes, olefins, and cyano-substituted olefins and isomers thereof.

In some instances, aryl and heteroaryl co-monomers which find use in the subject multichromophores are selected from a'-k' having the structure:

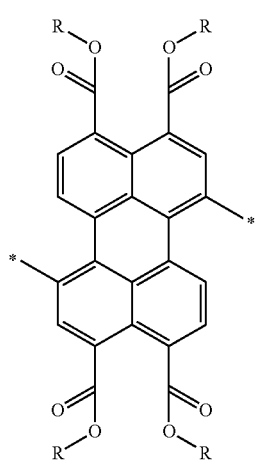
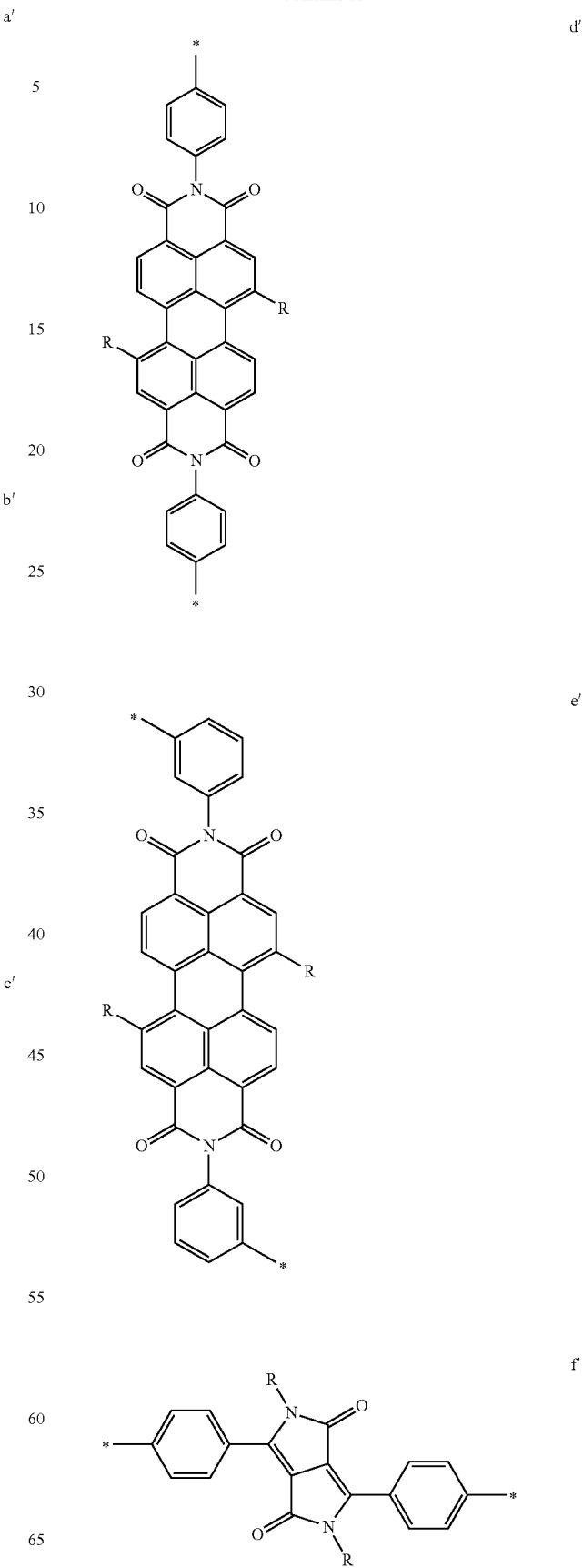

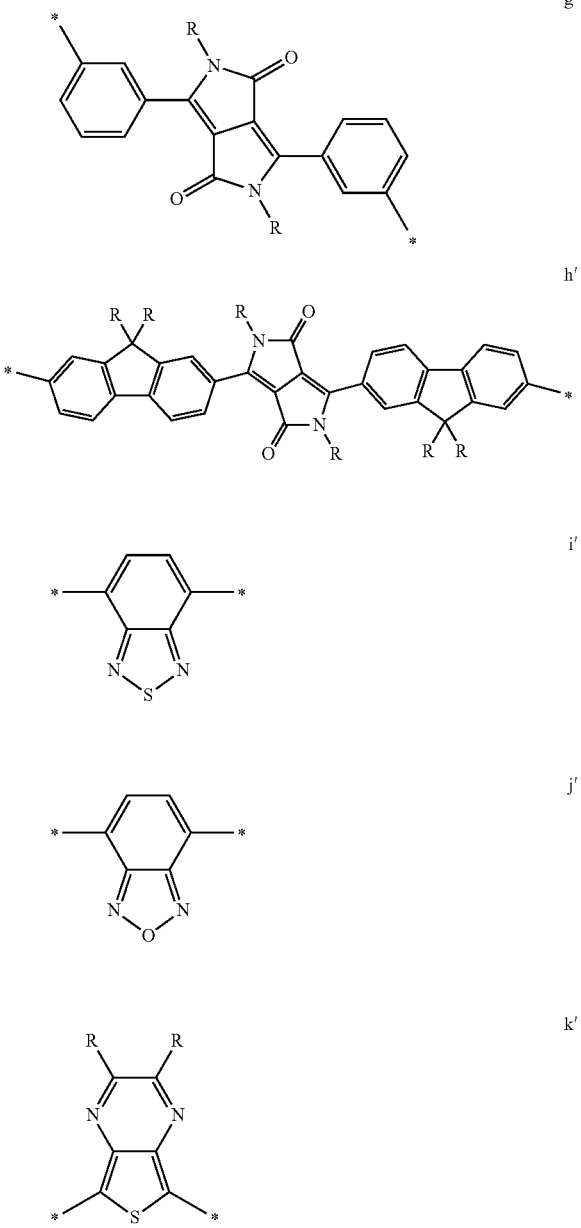

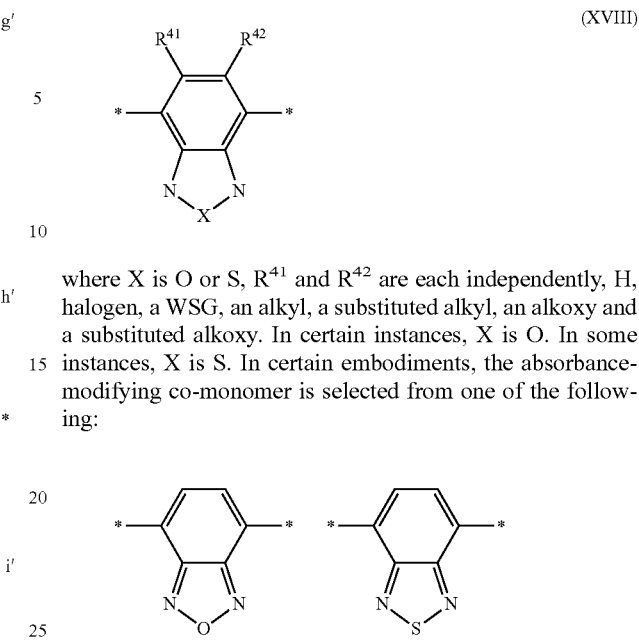

where X is O or S, $R^{41}$ and $R^{42}$ are each independently, H, halogen, a WSG, an alkyl, a substituted alkyl, an alkoxy and a substituted alkoxy. In certain instances, X is O. In some instances, X is S. In certain embodiments, the absorbance-modifying co-monomer is selected from one of the following:

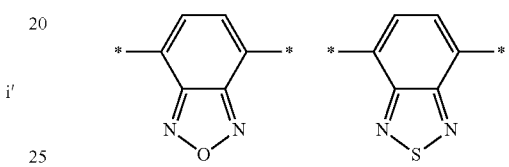

wherein *=site for covalent attachment to unsaturated backbone.

In some instances, the absorbance-modifying co-monomer is a substituted or unsubstituted phenyl, biphenyl or pyridyl co-monomer. In certain embodiments, the absorbance-modifying co-monomer is an optionally substituted aryl or heteroaryl co-monomer selected from the group consisting of substituted or unsubstituted 1,4-phenyl, a substituted or unsubstituted 1,3-phenyl, a substituted or unsubstituted 4,4'-biphenyl, a substituted or unsubstituted 2,5-pyridyl, and a substituted or unsubstituted 2,6-pyridyl. In certain instances, the absorbance-modifying co-monomer is an optionally substituted aryl or heteroaryl co-monomer selected from one of the following structures:

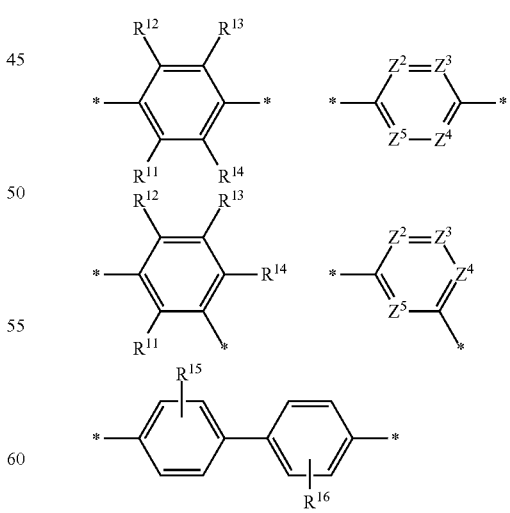

wherein *=a site for covalent attachment to unsaturated backbone and each R is independently H, a non-ionic side group capable of imparting solubility in water (e.g., a WSG), or -$L^2$-$Z^2$, where $L^2$ is a linker and $Z^2$ is a chemoselective tag or a linked metal complex. In certain instances of a'-k', each R is an alkyl or a benzyl substituted with one or more $(CH_2)_x(OCH_2CH_2)_yOCH_3$ where each x is independently an integer from 0-20, each y is independently an integer from 0 to 50. In certain instances of a'-k', each R is $(CH_2)_3(OCH_2CH_2)_{11}OCH_3$.

In certain embodiments, the multichromophore of formula (X) includes an absorbance-modifying co-monomer having the structure of one of co-monomers a'-k', as described herein. In some embodiments, the multichromophore of formula (X) includes an absorbance-modifying co-monomer having the formula (XVIII):

where $Z^2$-$Z^5$ are each independently CR or N, where at least one $Z^2$-$Z^5$ is N; and each R and each $R^{11}$-$R^{16}$ are independently selected from the group consisting of hydrogen, water solubilizing group, halogen, cyano, alkoxy, substituted alkoxy, alkyl and substituted alkyl. In certain embodiments, one and only one of $Z^2$-$Z^5$ is N. In certain embodiments, two and only two of $Z^2$-$Z^5$ is N. In certain instances, $R^{11}$, $R^{12}$, and $R^{14}$ are each H. In some instances, $R^{12}$ and $R^{14}$ are each H. In some instances, $R^{11}$ and $R^{13}$ are each H. In some cases, $R^{15}$ and $R^{16}$ are each H. In some instances, the halogen is fluoro.

In some cases, the absorbance-modifying co-monomer is an optionally substituted aryl or heteroaryl co-monomer selected from one of the following:

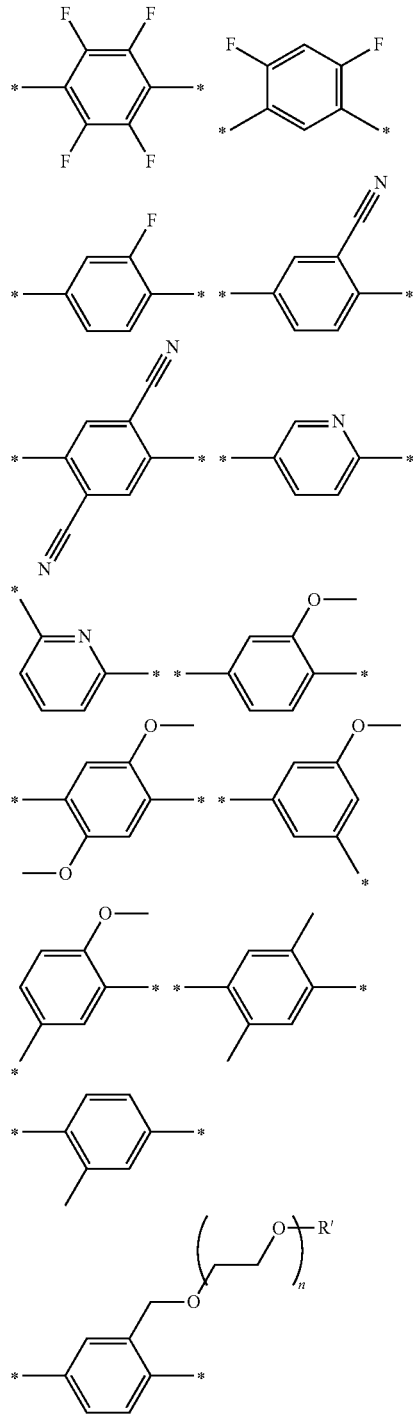

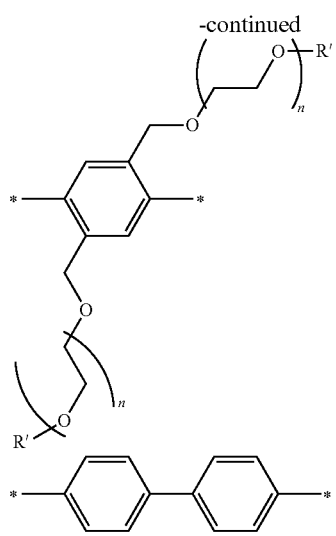

where n is 1-20 and R' is H or lower alkyl. In some embodiments of the substituted aryl or heteroaryl co-monomer structures, n is an integer from 3 to 20. In some embodiments, the multichromophore includes a substituted aryl co-monomer described by the following structure:

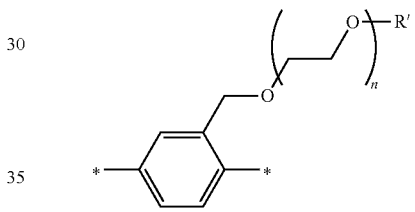

where n is 1-20 and R' is H or lower alkyl. In certain instances, n is 3 to 12. In some embodiments, the multichromophore includes a substituted aryl co-monomer described by the following structure:

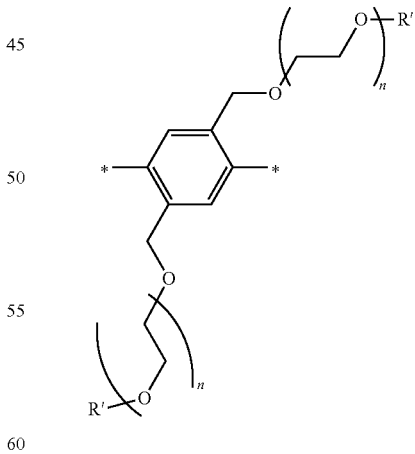

where each n is independently 1-20 and each R' is independently H or lower alkyl. In certain embodiments of the substituted aryl or heteroaryl co-monomer structures shown above, n is 3. In certain instances, R' is methyl. In certain instances, R' is hydrogen. In some embodiments, the multichromophore includes a substituted aryl co-monomer described by the following structure:

In some embodiments, the multichromophore includes a substituted aryl co-monomer described by the following structure:

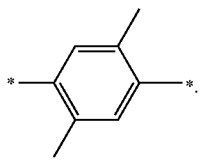

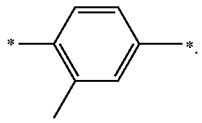

Any of the absorbance-modifying co-monomers described above may be utilized in the subject multichromophores, e.g., multichromophores of formulae (X) and (XIX)-(XX).

In some embodiments, the polymeric tandem dye is described by formula (XIX):

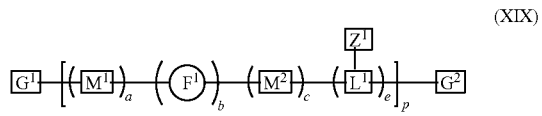

(XIX)

where $F^1$, $M^1$, $M^2$, a, b, c, e, $L^1$, $Z^1$, p, $G^1$ and $G^2$ are as described for formula (X). In some instances of formula (XIX), $F^1$ is a fluorene co-monomer. In certain instances of formula (XIX), $F^1$ is a carbazole co-monomer. In some embodiments of formula (XIX), $L^1$ is a fluorene co-monomer. In certain embodiments of formula (XIX), $L^1$ is a carbazole co-monomer. In some embodiments of formula (XIX), $L^1$ is a substituted aryl or heteroaryl co-monomer. In some embodiments of formula (XIX), $M^1$ and $M^2$ are each in dependently an absorbance modifying co-monomer (e.g., as described herein).

In some instances of formula (XIX), a and c are each 0 and b and e are each 1. In some instances of formula (XIX), b is 1 and a+c 1. In certain instances of formula (XIX), a+c=1 (e.g., a is 1 and c is 0, or a is 0 and c is 1). In certain embodiments of formula (XIX), a+c=2. In some cases of formula (XIX), $F^1$ is a fluorene co-monomer and $L^1$ is a substituted aryl or heteraryl co-monomer. In some cases of formula (XIX), $F^1$ and $L^1$ are independently a fluorene co-monomer. In some instances of formula (XIX), $G^1$ is a terminal group; and $G^2$ is a terminal group, a linker or a linked specific binding member. In certain cases, $G^2$ is a linked specific binding member. In some cases, $G^2$ is a linker, where the linker may include a chemoselective tag.

In some instances of formula (XIX):
a and c are each 0 and b and e are each 1;
$F^1$ is a fluorene co-monomer of formula (XIV) where each $R^2$ is independently an alkyl substituted with a water solubilizing group, such as each $R^2$ is —$(CH_2)x(OCH_2CH_2)yOCH_3$ where each x is independently 0 or an integer from 1-20, each y is independently 0 or an integer from 1 to 50;
$L^1$ is a fluorene co-monomer of formula (XV) where $R^3$ is an alkyl or an aralkyl substituted with a water solubilizing group (e.g., a PEG substituted alkyl or aralkyl), and $R^4$ is $L^2$-$Z^2$ wherein $L^2$ is a linker and $Z^2$ is a chemoselective tag (e.g., an amino group, —$NH_2$) or a linked metal complex ($Z^1$);
at least one of $G^1$ and $G^2$ is a substituted aryl group, e.g., an aryl group substituted with a linker (e.g., a C1-C6 alkyl linker) terminated with a carboxylic acid functional group or a linked specific binding member (e.g., as described herein).

In some instances, the multichromophore is described by formula (XX):

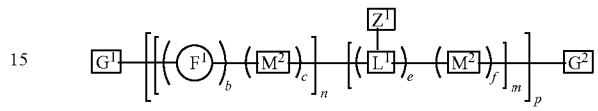

(XX)

where $F^1$, $M^2$, b, c, e, f, $L^1$, $Z^1$, n, m, p, $G^1$ and $G^2$ are as described for formula (X). In some instances of formula (XX), $F^1$ is a fluorene co-monomer. In certain instances of formula (XX), $F^1$ is a carbazole co-monomer. In some embodiments of formula (XIX), $L^1$ is a fluorene co-monomer. In some embodiments of formula (XX), $L^1$ is a substituted aryl or heteroaryl co-monomer. In some embodiments of formula (XX), $M^1$ and $M^2$ are each in dependently an absorbance modifying co-monomer (e.g., as described herein).

In some embodiments of formula (XX), b is 1; c is 0 or 1; e is 1; f is 0 or 1; $G^1$ is a terminal group; and $G^2$ is a terminal group, a linker or a linked specific binding member. In certain instances of formula (XX), c is 1. In certain cases of formula (XX), c is 0. In certain instances of formula (XX), f is 1. In certain cases of formula (XX), f is 0. In certain cases, $G^2$ is a linked specific binding member. In some cases, $G^2$ is a linker, where the linker may include a chemoselective tag.

In some instances of formula (XX):
c and f are each 0 and b and e are each 1;
$F^1$ is a fluorene co-monomer of formula (XIV) where each $R^2$ is independently an alkyl substituted with a water solubilizing group, such as each $R^2$ is —$(CH_2)x(OCH_2CH_2)yOCH_3$ where each x is independently 0 or an integer from 1-20, each y is independently 0 or an integer from 1 to 50;
$L^1$ is a fluorene co-monomer of formula (XV) where $R^3$ is an alkyl or an aralkyl substituted with a water solubilizing group (e.g., a PEG substituted alkyl or aralkyl), and $R^4$ is $L^2$-$Z^2$ wherein $L^2$ is a linker and $Z^2$ is a chemoselective tag (e.g., an amino group, —$NH_2$) or a linked metal complex ($Z^1$);
at least one of $G^1$ and $G^2$ is a substituted aryl group, e.g., an aryl group substituted with a linker (e.g., a C1-C6 alkyl linker) terminated with a carboxylic acid functional group or a linked specific binding member (e.g., as described herein).

In some instances of formulae (X) and (XIX) to (XX), $L^1$ is described by the structure:

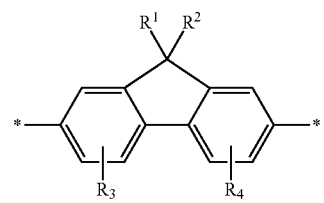

wherein:

$R^1$ is a substituent including a water solubilizing group (e.g., a PEG substituted alkyl);

$R^2$ is $L^2$-$Z^2$ wherein $L^2$ is a linker and $Z^2$ is the acceptor metal complex; and $R^3$ and $R^4$ are independently selected from the group consisting of H, a water solubilizing group, an alkyl, a substituted alkyl, an alkoxy, a substituted alkoxy, a halogen and a nitro. In certain instances, $R^3$ and $R^4$ are each hydrogen.

In some embodiments of formulae (X) and (XIX) to (XX), at least one of $G^1$ and $G^2$ is -$L^3$-$Z^4$ where $L^3$ is a linker (e.g., as described herein) and $Z^4$ is a specific binding member (e.g., as described herein). In some embodiments of formulae (X) and (XIX) to (XX), at least one of $G^1$ and $G^2$ is -$L^3$-$Z^3$ where $L^3$ is a linker (e.g., as described herein) and $Z^3$ is a chemoselective tag (e.g., as described herein). In some instances, $Z^3$ is selected from the group consisting of carboxylic acid, active ester (e.g., N-hydroxy succinimidyl ester (NHS) or sulfo-NHS), amino, maleimide, iodoacetyl and thiol. In certain embodiments of formulae (X) and (XIX) to (XX), at least one of $G^1$ and $G^2$ is described by the following structure:

\*-Ar-L-Z where Ar is a π-conjugated aryl group, L is a linker and Z is a chemoselective tag or a specific binding member. In certain embodiments of formulae (X) and (XIX) to (XX), at least one of $G^1$ and $G^2$ is described by the following structure:

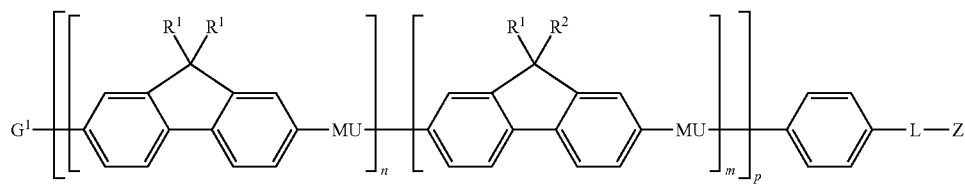

wherein:

q is 0 or an integer from 1-12;

L is an optional linker; and

Z is a chemoselective tag or a specific binding member.

In certain embodiments, Z is a biomolecule. Biomolecules of interest include, but are not limited to, polypeptides, polynucleotides, carbohydrates, fatty acids, steroids, purines, pyrimidines, derivatives, structural analogs thereof and combinations thereof. In certain instances, Z is an antibody. In some instances, Z is an antibody fragment or binding derivative thereof. In some cases, the antibody fragment or binding derivative thereof is selected from the group consisting of a Fab fragment, a F(ab')$_2$ fragment, a scFv, a diabody and a triabody.

In some embodiments, the polymeric tandem dye is described by formula (XXI):

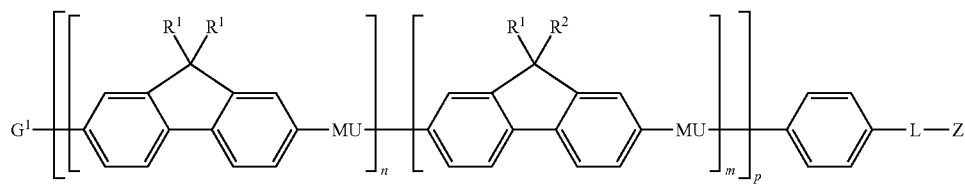

(XXI)

where: each $R^1$ is independently an alkyl or aralkyl substituted with one or more WSG, or a branching group further substituted with two or more WSGs; MU is an absorbance modifying co-monomer (e.g., as described herein); $R^2$ is $L^2$-$Z^2$ wherein $L^2$ is a linker and $Z^2$ is the acceptor luminescent metal complex; L is a linker and Z is a chemoselective tag or a linked specific binding member; $G^1$ is an end group; and n, m and p are each independently an integer from 1 to 100,000. In some instances, $G^1$ is an aryl end group. In some cases, $G^1$ is a phenyl. In certain embodiments, Z is selected from a carboxylic acid, an amino or a maleimide. In certain instances, Z is a linked specific binding member. In some instances, L is an alkyl-carboxylic acid, such as —(CH$_2$)$_3$COOH. In certain embodiments, one or more of the $R^1$ groups is a branching group further substituted with two or more WSGs. In certain instances, the branching group is a substituted aralkyl, such as a substituted benzyl group, which is disubstituted with two PEG groups.

In some embodiments, the polymeric tandem dye is described by formula (XXIII):

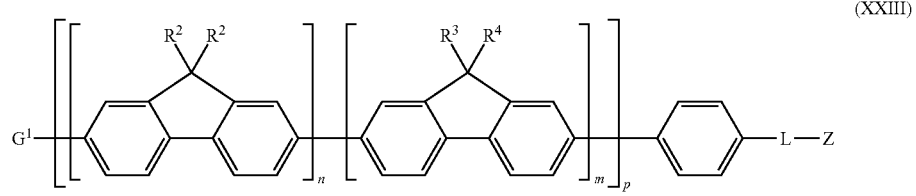

(XXIII)

where: each $R^2$ is independently an alkyl or aralkyl substituted with one or more WSG, or a branching group further substituted with two or more WSGs; $R^3$ is an alkyl or a substituted alkyl (e.g., as described herein); $R^4$ is $L^2$-$Z^2$ wherein $L^2$ is a linker and $Z^2$ is the acceptor luminescent metal complex; L is a linker and Z is a chemoselective tag or a linked specific binding member; $G^1$ is an end group; and n, m and p are each independently an integer from 1 to 100,000. In some instances, $G^1$ is an aryl end group. In some cases, $G^1$ is a phenyl. In certain embodiments, Z is selected from a carboxylic acid, an amino or a maleimide. In certain instances, Z is a linked specific binding member. In some instances, L-Z is an alkyl-carboxylic acid, such as —$(CH_2)_3$COOH. In certain embodiments, one or more of the $R^2$ groups is a branching group further substituted with two or more WSGs. In certain instances, the branching group is a substituted aralkyl, such as a substituted benzyl group, which is disubstituted with two PEG groups. In some instances of formula (XXIII): each $R^2$ is independently an alkyl substituted with a water solubilizing group, such as each $R^2$ is —$(CH_2)x(OCH_2CH_2)yOCH_3$ where each x is independently 0 or an integer from 1-20, each y is independently 0 or an integer from 1 to 50; $R^3$ is an alkyl or an aralkyl substituted with a water solubilizing group (e.g., a PEG substituted alkyl or aralkyl), and $R^4$ is $L^2$-$Z^2$ wherein $L^2$ is a linker and $Z^2$ is a chemoselective tag (e.g., an amino group, —$NH_2$) or a linked metal complex ($Z^1$). In some embodiments, the polymeric tandem dye is described by formula (XXIV):

as described herein); L is a linker and $Z^1$ is a linked metal complex; $G^1$ and $G^2$ are each independently an end group; and w, x, y and z are the mol % values of the co-monomers in the conjugated polymer. In some instances, $G^1$ is an aryl end group. In some cases, $G^1$ is a substituted phenyl. In certain instances, $G^1$ or $G^2$ comprise a linked specific binding member. In some instances, L comprises an alkyl-amido, such as —$(CH_2)_3$CONH—. In certain embodiments, each $R^1$ group is a branching group further substituted with two or more WSGs. In certain instances, the branching group is a substituted aralkyl, such as a substituted benzyl group, which is substituted with two PEG groups.

In some instances of formula (XXII), w is 10 mol % or more, such as 15 mol % or more, 20 mol % or more, 25 mol % or more, or even more. In some instances of formula (XXII), x is 0. In some instances of formula (XXII), x is 10 mol % or more, such as 15 mol % or more, 20 mol % or more, 25 mol % or more, or even more. In some instances of formula (XXII), y is 0. In some instances of formula (XXII), y is 10 mol % or more, such as 15 mol % or more, 20 mol % or more, 25 mol % or more, or even more. In some instances of formula (XXII), z is 10 mol % or more, such as 15 mol % or more, 20 mol % or more, 25 mol % or more, or even more.

In some instances of the multichromophores of any one of formulae (X), (XVII) and (XIX)-(XXIV), the mol % of the luminescent metal complex acceptor units in the multichro-

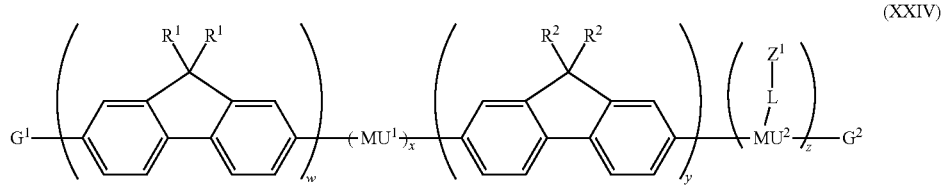

(XXIV)

where: each $R^1$ and each $R^2$ is independently an alkyl substituted with a WSG (e.g., as described herein), or a branching group further substituted with two or more WSGs (e.g., as described herein); $MU^1$ and $MU^2$ are independently an absorbance modifying co-monomer (e.g., as described herein); L is a linker and $Z^1$ is a linked metal complex; $G^1$ and $G^2$ are each independently an end group; and w, x, y and z are the mol % values of the co-monomers in the conjugated polymer.

In some embodiments, the polymeric tandem dye is described by formula (XXII):

mophore (e.g., the mol % of linking co-monomers to which luminescent metal complexes are linked in the donor water soluble light harvesting) ranges from 1 mol % to 50 mol %, such as from 5 mol % to 25 mol % or from 10 mol % to 25 mol %; or such as from 5 mol % to 25 mol % or from 10 mol % to 25 mol %; or such as from 1 mol % to 25 mol %, from 1 mol % to 10 mol %, or from 1 mol % to 5 mol %.

It is understood that for any of the structures and formula depicted herein that in some cases of the subject multichromophore the end groups depicted may be located at the opposite ends to those shown, e.g., the end groups $G^1$ and

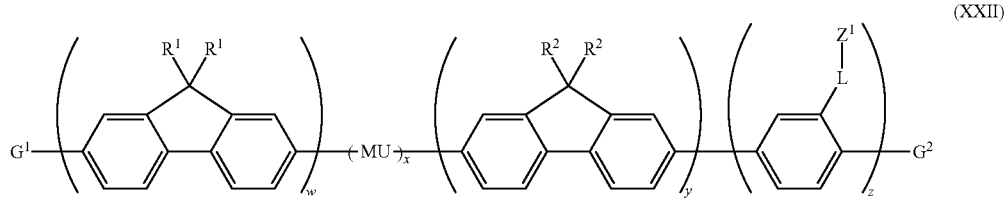

(XXII)

where: each $R^1$ and each $R^2$ is independently an alkyl substituted with a WSG, or a branching group further substituted with two or more WSGs (e.g., as described herein); MU is an absorbance modifying co-monomer (e.g., -Ph-L-Z may be switched. In some embodiments of the multichromophores described herein (e.g., formulae (X), (XVII) and (XIX)-(XXIV), at least one of $G^1$ and $G^2$ is selected from one of the following structures 1-33:

| 41 | 42 |
|---|---|
| 1<br>*—H | 2<br>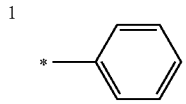 |
| 3<br>*—Br | 4<br>*—Cl |
| 5<br>*—I | 6<br>*—SH |
| 7<br>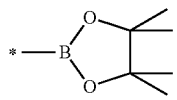 | 8<br>*—B(OH)$_2$ |
| 9<br>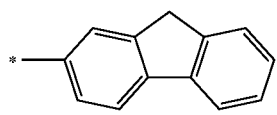 | 10<br>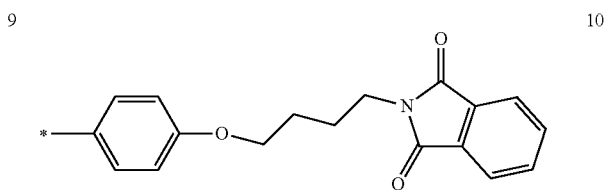 |
| 11<br>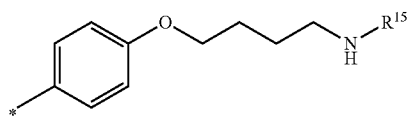 | 12<br>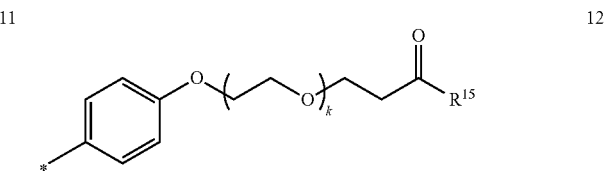 |
| 13<br>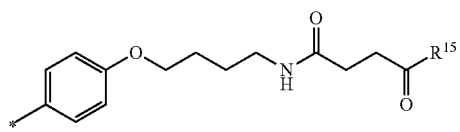 | 14<br>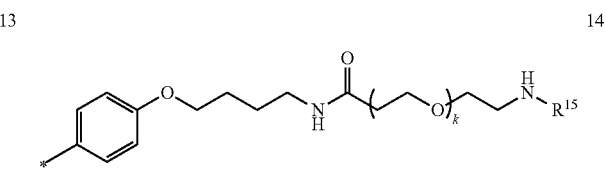 |
| 15<br>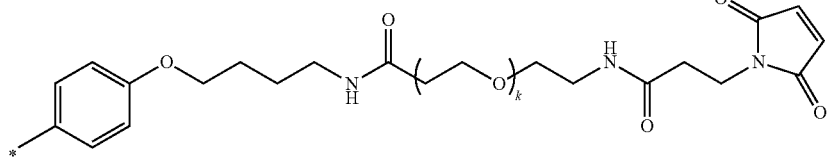 | |
| 16<br>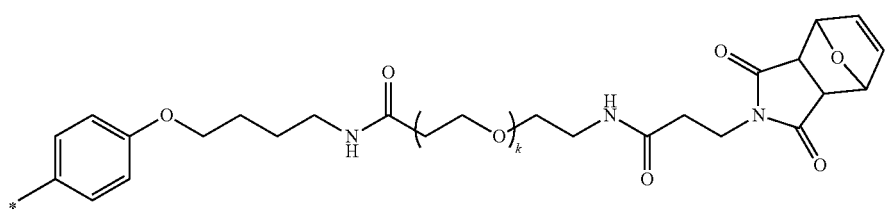 | |
| 17<br>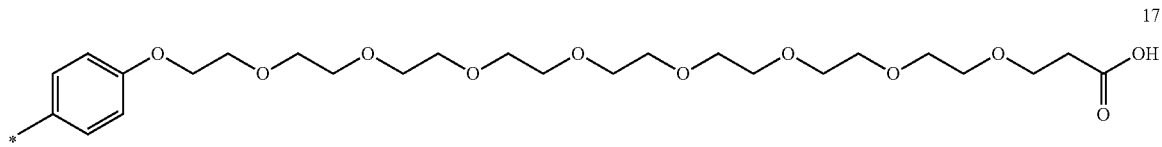 | |
| 18<br> | 19<br>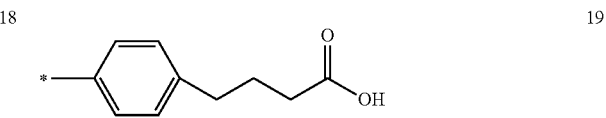 |

-continued
20
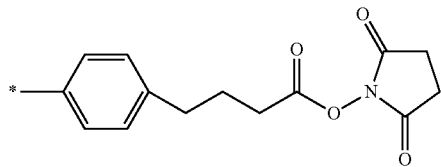
21
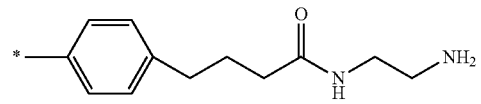
22
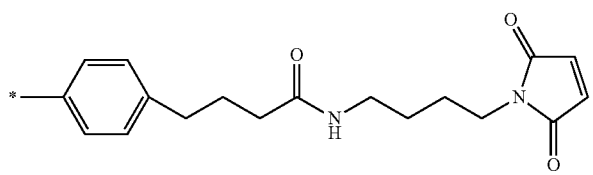
23
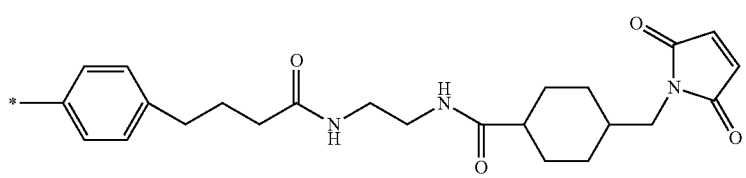
24
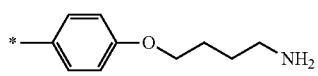
25
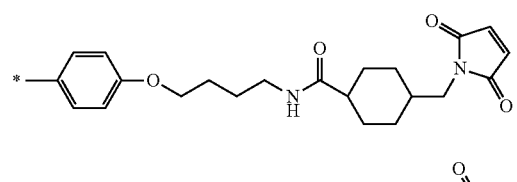
26
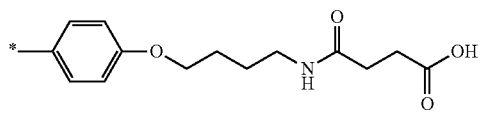
27
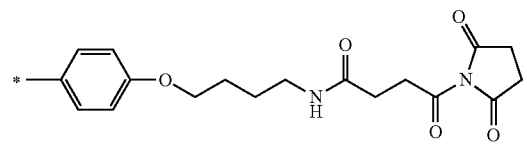
28
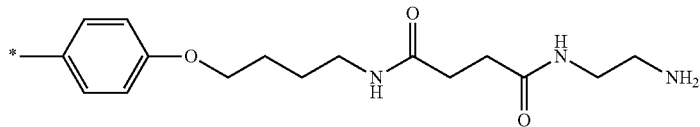
29
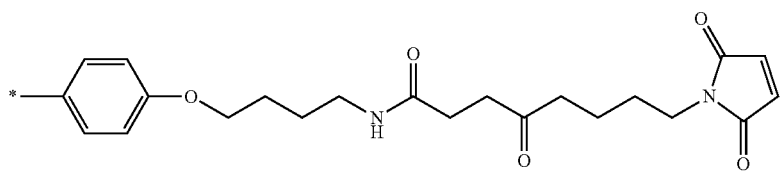
30
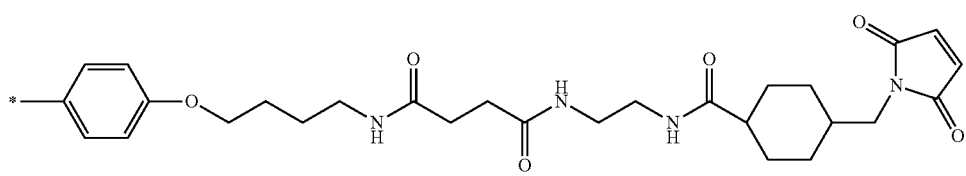
31
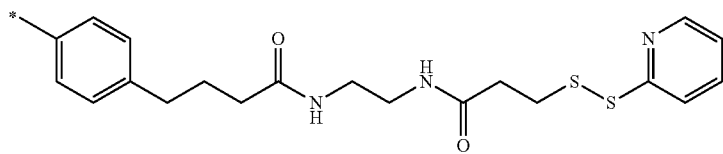

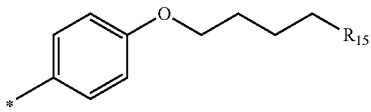

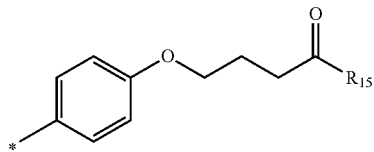

*=site for covalent attachment to unsaturated backbone;

wherein R' is independently H, halogen, $C_1$-$C_{12}$ alkyl, ($C_1$-$C_{12}$ alkyl)$NH_2$, $C_2$-$C_{12}$ alkene, $C_2$-$C_{12}$ alkyne, $C_3$-$C_{12}$cycloalkyl, $C_1$-$C_{12}$ haloalkyl, $C_2$-$C_{18}$(hetero)aryl, $C_2$-$C_{18}$(hetero)arylamino, —[$CH_2$—$CH_2$]$_{r'}$—$Z^1$, or ($C_1$-$C_{12}$)alkoxy-$X^1$; and wherein $Z^1$ is —OH or —COOH; $X^1$ is —$NH_2$, —NHCOOH, —NHCOOC($CH_3$)$_3$, —NHCO(C3-C12)cycloalkyl(C1-C4)alkyl-N-maleimide; or —NHCO[$CH_2$—$CH_2$—O]$_{s'}$($CH_2$)$_{s'}$$NH_2$; r' is an integer from 1 to 20; and each s' is independently an integer from 1 to 20, ($CH_2$)$_3$($OCH_2CH_2$)$_{x''}$$OCH_3$ where x" is independently an integer from 0 to 50, or a benzyl optionally substituted with one or more halogen, hydroxyl, $C_1$-$C_{12}$ alkoxy, or ($OCH_2CH_2$)$_{y''}$$CH_3$ where each y" is independently an integer from 0 to 50 and R' is different from R;

wherein k is 2, 4, 8, 12 or 24;

wherein $R^{15}$ is selected from the group consisting of I-u having the structure:

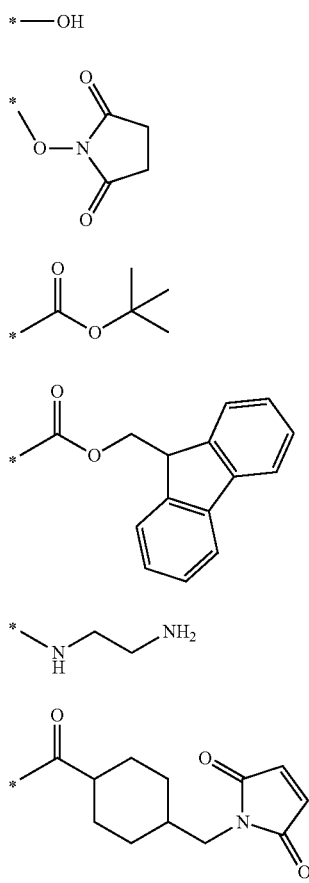

*=site for covalent attachment to backbone.

Labelled Specific Binding Members

Aspects of the present disclosure include labelled specific binding members. A labelled specific binding member is a conjugate of a subject polymeric tandem dye (e.g., as described herein) and a specific binding member. Any of the polymeric tandem dyes described herein may be conjugated to a specific binding member. The specific binding member and the polymeric tandem dye can be conjugated (e.g., covalently linked) to each other at any convenient locations of the two molecules, via an optional linker.

As used herein, the term "specific binding member" refers to one member of a pair of molecules which have binding specificity for one another. One member of the pair of molecules may have an area on its surface, or a cavity, which specifically binds to an area on the surface of, or a cavity in, the other member of the pair of molecules. Thus the members of the pair have the property of binding specifically to each other to produce a binding complex. In some embodiments, the affinity between specific binding members in a binding complex is characterized by a $K_d$ (dissociation constant) of $10^{-6}$ M or less, such as $10^{-7}$ M or less, including $10^{-8}$ M or less, e.g., $10^{-9}$ M or less, $10^{-10}$ M or less, $10^{-11}$ M or less, $10^{-12}$ M or less, $10^{-13}$ M or less, $10^{-14}$ M or less, including $10^{-15}$ M or less. In some embodiments, the specific binding members specifically bind with high avidity. By high avidity is meant that the binding member specifically binds with an apparent affinity characterized by an apparent $K_d$ of $10 \times 10^{-9}$ M or less, such as $1 \times 10^{-9}$ M or less, $3 \times 10^{-10}$ M or less, $1 \times 10^{-10}$ M or less, $3 \times 10^{-11}$ M or less, $1 \times 10^{-11}$ M or less, $3 \times 10^{-12}$ M or less or $1 \times 10^{-12}$ M or less.

The specific binding member can be proteinaceous. As used herein, the term "proteinaceous" refers to a moiety that is composed of amino acid residues. A proteinaceous moiety can be a polypeptide. In certain cases, the proteinaceous specific binding member is an antibody. In certain embodiments, the proteinaceous specific binding member is an antibody fragment, e.g., a binding fragment of an antibody that specific binds to a polymeric dye. As used herein, the terms "antibody" and "antibody molecule" are used interchangeably and refer to a protein consisting of one or more polypeptides substantially encoded by all or part of the recognized immunoglobulin genes. The recognized immunoglobulin genes, for example in humans, include the kappa (k), lambda (l), and heavy chain genetic loci, which together comprise the myriad variable region genes, and the constant region genes mu (u), delta (d), gamma (g), sigma (e), and alpha (a) which encode the IgM, IgD, IgG, IgE, and IgA isotypes respectively. An immunoglobulin light or heavy chain variable region consists of a "framework" region (FR) interrupted by three hypervariable regions, also called "complementarity determining regions" or "CDRs". The extent of the framework region and CDRs have been precisely defined (see, "Sequences of Proteins of Immunological Interest," E. Kabat et al., U.S. Department of Health and Human Services, (1991)). The numbering of all antibody amino acid sequences discussed herein conforms to the Kabat system. The sequences of the framework regions of different light or heavy chains are relatively conserved within a species. The framework region of an antibody, that is the combined framework regions of the constituent light and heavy chains, serves to position and align the CDRs. The CDRs are primarily responsible for binding to an epitope of an antigen. The term antibody is meant to include full length antibodies and may refer to a natural antibody from any organism, an engineered antibody, or an antibody generated recombinantly for experimental, therapeutic, or other purposes as further defined below.

Antibody fragments of interest include, but are not limited to, Fab, Fab', F(ab')2, Fv, scFv, or other antigen-binding subsequences of antibodies, either produced by the modification of whole antibodies or those synthesized de novo using recombinant DNA technologies. Antibodies may be monoclonal or polyclonal and may have other specific activities on cells (e.g., antagonists, agonists, neutralizing, inhibitory, or stimulatory antibodies). It is understood that the antibodies may have additional conservative amino acid substitutions which have substantially no effect on antigen binding or other antibody functions.

In certain embodiments, the specific binding member is a Fab fragment, a F(ab')$_2$ fragment, a scFv, a diabody or a triabody. In certain embodiments, the specific binding member is an antibody. In some cases, the specific binding member is a murine antibody or binding fragment thereof. In certain instances, the specific binding member is a recombinant antibody or binding fragment thereof.

In some embodiments, the labelled specific binding member includes: a water soluble light harvesting multichromophore (e.g., as described herein) comprising a conjugated segment including: a fused 6-5-6 tricyclic co-monomer (e.g., a fluorene co-monomer, as described herein); and a luminescent metal complex covalently linked to the multichromophore in energy-receiving proximity therewith (e.g., as described herein); and a specific binding member covalently linked to the multichromophore.

In some instances of the labelled specific binding member, the multichromophore is described by any one of formulae (X) and (XIX)-(XII) (e.g., as described herein), wherein: $G^1$ and $G^2$ are each independently selected from the group consisting of a terminal group (e.g., end group), a π conjugated segment, a linker and a linked specific binding member, wherein at least one of $G^1$ and $G^2$ is a linked specific binding member. In some instances, $F^1$ is a fluorene co-monomer.

Methods

As summarized above, aspects of the invention include methods of evaluating a sample for the presence of a target analyte. Aspects of the method include contacting the sample with a polymeric dye conjugate that specifically binds the target analyte to produce a labelling composition contacted sample. As used herein, the terms "polymeric dye conjugate" and "labelled specific binding member" are used interchangeably. As such, the polymeric dye conjugate can include: (i) a water soluble light harvesting multichromophore (e.g., as described herein) including a conjugated segment including: a fused 6-5-6 tricyclic co-monomer (e.g., a fluorene co-monomer, as described herein); and a luminescent metal complex covalently linked to the multichromophore in energy-receiving proximity therewith (e.g., as described herein); and (ii) a specific binding member (e.g., as described herein).

Any convenient method may be used to contact the sample with a polymeric dye conjugate that specifically binds to the target analyte to produce the labelling composition contacted sample. In some instances, the sample is contacted with the polymeric dye conjugate under conditions in which the specific binding member specifically binds to the target analyte, if present. For specific binding of the specific binding member of the conjugate with the target analyte, an appropriate solution may be used that maintains the biological activity of the components of the sample and the specific binding member. The solution may be a balanced salt solution, e.g., normal saline, PBS, Hank's balanced salt solution, etc., conveniently supplemented with fetal calf serum, human platelet lysate or other factors, in conjunction with an acceptable buffer at low concentration, such as from 5-25 mM. Convenient buffers include HEPES, phosphate buffers, lactate buffers, etc. Various media are commercially available and may be used according to the nature of the target analyte, including dMEM, HBSS, dPBS, RPMI, Iscove's medium, etc., in some cases supplemented with fetal calf serum or human platelet lysate. The final components of the solution may be selected depending on the components of the sample which are included.

The temperature at which specific binding of the specific binding member of the conjugate to the target analyte takes place may vary, and in some instances may range from 5° C. to 50° C., such as from 10° C. to 40° C., 15° C. to 40° C., 20° C. to 40° C., e.g., 20° C., 25° C., 30° C., 35° C. or 37° C. (e.g., as described above). In some instances, the temperature at which specific binding takes place is selected to be compatible with the biological activity of the specific binding member and/or the target analyte. In certain instances, the temperature is 25° C., 30° C., 35° C. or 37° C. In certain cases, the specific binding member is an antibody or fragment thereof and the temperature at which specific binding takes place is room temperature (e.g., 25° C.), 30° C., 35° C. or 37° C. Any convenient incubation time for specific binding may be selected to allow for the formation of a desirable amount of binding complex, and in some instances, may be 1 minute (min) or more, such as 2 min or more, 10 min or more, 30 min or more, 1 hour or more, 2 hours or more, or even 6 hours or more.

Any convenient specific binding members may be utilized in the conjugate. Specific binding members of interest include, but are not limited to, those agents that specifically bind cell surface proteins of a variety of cell types, including but not limited to, stem cells, e.g., pluripotent stem cells, hematopoietic stem cells, T cells, T regulator cells, dendritic cells, B Cells, e.g., memory B cells, antigen specific B cells, granulocytes, leukemia cells, lymphoma cells, virus cells (e.g., HIV cells) NK cells, macrophages, monocytes, fibroblasts, epithelial cells, endothelial cells, and erythroid cells. Target cells of interest include cells that have a convenient cell surface marker or antigen that may be captured by a convenient specific binding member conjugate. In some embodiments, the target cell is selected from HIV containing cell, a Treg cell, an antigen-specific T-cell populations, tumor cells or hematopoetic progenitor cells (CD34+) from whole blood, bone marrow or cord blood. Any convenient cell surface proteins or cell markers may be targeted for specific binding to polymeric dye conjugates in the subject methods. In some embodiments, the target cell includes a cell surface marker selected from a cell receptor and a cell surface antigen. In some cases, the target cell may include a cell surface antigen such as CD11b, CD123, CD14, CD15, CD16, CD19, CD193, CD2, CD25, CD27, CD3, CD335, CD36, CD4, CD43, CD45RO, CD56, CD61, CD7, CD8, CD34, CD1c, CD23, CD304, CD235a, T cell receptor alpha/beta, T cell receptor gamma/delta, CD253, CD95, CD20, CD105, CD117, CD120b, Notch4, Lgr5 (N-Terminal), SSEA-3, TRA-1-60 Antigen, Disialoganglioside GD2 and CD71.

Any convenient targets may be selected for evaluation utilizing the subject methods. Targets of interest include, but are not limited to, a nucleic acid, such as an RNA, DNA, PNA, CNA, HNA, LNA or ANA molecule, a protein, such as a fusion protein, a modified protein, such as a phosphorylated, glycosylated, ubiquitinated, SUMOylated, or acetylated protein, or an antibody, a peptide, an aggregated biomolecule, a cell, a small molecule, a vitamin and a drug molecule. As used herein, the term "a target protein" refers to all members of the target family, and fragments thereof. The target protein may be any protein of interest, such as a therapeutic or diagnostic target, including but not limited to: hormones, growth factors, receptors, enzymes, cytokines, osteoinductive factors, colony stimulating factors and immunoglobulins. The term "target protein" is intended to include recombinant and synthetic molecules, which can be prepared using any convenient recombinant expression methods or using any convenient synthetic methods, or purchased commercially. In some embodiments, the polymeric dye conjugates include an antibody or antibody fragment. Any convenient target analyte that specifically binds an antibody or antibody fragment of interest may be targeted in the subject methods.

In some embodiments, the target analyte is associated with a cell. In certain instances, the target analyte is a cell surface marker of the cell. In certain cases, the cell surface marker is selected from the group consisting of a cell receptor and a cell surface antigen. In some instances, the target analyte is an intracellular target, and the method further includes lysing the cell.

In some embodiments, the sample may include a heterogeneous cell population from which target cells are isolated. In some instances, the sample includes peripheral whole blood, peripheral whole blood in which erythrocytes have been lysed prior to cell isolation, cord blood, bone marrow, density gradient-purified peripheral blood mononuclear cells or homogenized tissue. In some cases, the sample includes hematopoetic progenitor cells (e.g., CD34+ cells) in whole blood, bone marrow or cord blood. In certain embodiments, the sample includes tumor cells in peripheral blood. In certain instances, the sample is a sample including (or suspected of including) viral cells (e.g., HIV).

The labelled specific binding members find use in the subject methods, e.g., for labeling a target cell, particle, target or analyte with a polymeric dye or polymeric tandem dye. For example, labelled specific binding members find use in labeling cells to be processed (e.g., detected, analyzed, and/or sorted) in a flow cytometer. The labelled specific binding members may include antibodies that specifically bind to, e.g., cell surface proteins of a variety of cell types (e.g., as described herein). The labelled specific binding members may be used to investigate a variety of biological (e.g., cellular) properties or processes such as cell cycle, cell proliferation, cell differentiation, DNA repair, T cell signaling, apoptosis, cell surface protein expression and/or presentation, and so forth. Labelled specific binding members may be used in any application that includes (or may include) antibody-mediated labeling of a cell, particle or analyte.

In some instances of the method, the labelled specific binding member includes a multichromophore according to any one of formulae (X) and (XIX)-(XII) (e.g., as described herein), wherein: $G^1$ and $G^2$ are each independently selected from the group consisting of a terminal group, a π conjugated segment, a linker and a linked specific binding member, wherein at least one of $G^1$ and $G^2$ is a linked specific binding member. In some instances, $F^1$ is a fluorene co-monomer.

Aspects of the method include assaying the labelling composition contacted sample for the presence of a polymeric dye conjugate-target analyte binding complex to evaluate whether the target analyte is present in the sample. Once the sample has been contacted with the polymeric dye conjugate, any convenient methods may be utilized in assaying the labelling composition contacted sample that is produced for the presence of a polymeric dye conjugate-target analyte binding complex. The polymeric dye conjugate-target analyte binding complex is the binding complex that is produced upon specific binding of the specific binding member of the conjugate to the target analyte, if present. Assaying the labelling composition contacted sample can include detecting a fluorescent signal from the binding complex, if present. In some cases, the assaying includes a separating step where the target analyte, if present, is separated from the sample. A variety of methods can be utilized to separate a target analyte from a sample, e.g., via immobilization on a support. Assay methods of interest include, but are not limited to, any convenient methods and assay formats where pairs of specific binding members such as avidin-biotin or hapten-anti-hapten antibodies find use, are of interest. Methods and assay formats of interest that may be adapted for use with the subject compositions include, but are not limited to, flow cytometry methods, in-situ hybridization methods, enzyme-linked immunosorbent assays (ELISAs), western blot analysis, magnetic cell separation assays and fluorochrome purification chromatography.

In certain embodiments, the method further includes contacting the sample with a second specific binding member that specifically binds the target analyte. In certain instances, the second specific binding member is support bound. Any convenient supports may be utilized to immobilize a component of the subject methods (e.g., a second specific binding member). In certain instances, the support is a particle, such as a magnetic particle. In some instances, the second specific binding member and the polymeric dye conjugate produce a sandwich complex that may be isolated and detected, if present, using any convenient methods. In some embodiments, the method further includes flow cytometrically analyzing the polymeric dye conjugate-target analyte binding complex, i.e., a fluorescently labelled target analyte. Assaying for the presence of a polymeric dye conjugate-target analyte binding complex may provide assay results (e.g., qualitative or quantitative assay data) which can be used to evaluate whether the target analyte is present in the sample.

Any convenient supports may be utilized in the subject methods to immobilize any convenient component of the methods, e.g., labelled specific binding member, target, secondary specific binding member, etc. Supports of interest include, but are not limited to: solid substrates, where the substrate can have a variety of configurations, e.g., a sheet, bead, or other structure, such as a plate with wells; beads, polymers, particle, a fibrous mesh, hydrogels, porous matrix, a pin, a microarray surface, a chromatography support, and the like. In some instances, the support is selected from the group consisting of a particle, a planar solid substrate, a fibrous mesh, a hydrogel, a porous matrix, a pin, a microarray surface and a chromatography support. The support may be incorporated into a system that it provides for cell isolation assisted by any convenient methods, such as a manually-operated syringe, a centrifuge or an automated liquid handling system. In some cases, the support finds use in an automated liquid handling system for the high throughput isolation of cells, such as a flow cytometer.

In some embodiments of the method, the separating step includes applying an external magnetic field to immobilize a magnetic particle. Any convenient magnet may be used as a source of the external magnetic field (e.g., magnetic field gradient). In some cases, the external magnetic field is generated by a magnetic source, e.g. by a permanent magnet or electromagnet. In some cases, immobilizing the magnetic particles means the magnetic particles accumulate near the surface closest to the magnetic field gradient source, i.e. the magnet.

The separating may further include one or more optional washing steps to remove unbound material of the sample from the support. Any convenient washing methods may be used, e.g., washing the immobilized support with a biocompatible buffer which preserves the specific binding interaction of the polymeric dye and the specific binding member. Separation and optional washing of unbound material of the sample from the support provides for an enriched population of target cells where undesired cells and material may be removed.

In certain embodiments, the method further includes detecting the labelled target. Detecting the labelled target may include exciting the multichromophore with one or more lasers and subsequently detecting fluorescence emission from the polymeric tandem dye using one or more optical detectors. Detection of the labelled target can be performed using any convenient instruments and methods, including but not limited to, flow cytometry, FACS systems, fluorescence microscopy; fluorescence, luminescence, ultraviolet, and/or visible light detection using a plate reader; high performance liquid chromatography (HPLC); and mass spectrometry. When using fluorescently labeled components in the methods and compositions of the present disclosure, it is recognized that different types of fluorescence detection systems can be used to practice the subject methods. In some cases, high throughput screening can be performed, e.g., systems that use 96 well or greater microtiter plates. A variety of methods of performing assays on fluorescent materials can be utilized, such as those methods described in, e.g., Lakowicz, J. R., Principles of Fluorescence Spectroscopy, New York: Plenum Press (1983); Herman, B., Resonance energy transfer microscopy, in: Fluorescence Microscopy of Living Cells in Culture, Part B, Methods in Cell Biology, vol. 30, ed. Taylor, D. L. & Wang, Y.-L., San Diego: Academic Press (1989), pp. 219-243; Turro, N.J., Modern Molecular Photochemistry, Menlo Park: Benjamin/Cummings Publishing Col, Inc. (1978), pp. 296-361.

Fluorescence in a sample can be measured using a fluorimeter. In some cases, excitation radiation, from an excitation source having a first wavelength, passes through excitation optics. The excitation optics cause the excitation radiation to excite the sample. In response, fluorescently labelled targets in the sample emit radiation which has a wavelength that is different from the excitation wavelength. Collection optics then collect the emission from the sample. The device can include a temperature controller to maintain the sample at a specific temperature while it is being scanned. In certain instances, a multi-axis translation stage moves a microtiter plate holding a plurality of samples in order to position different wells to be exposed. The multi-axis translation stage, temperature controller, auto-focusing feature, and electronics associated with imaging and data collection can be managed by an appropriately programmed digital computer. The computer also can transform the data collected during the assay into another format for presentation.

In some embodiments, the method of evaluating a sample for the presence of a target analyte further includes detecting fluorescence in a flow cytometer. In some embodiments, the method of evaluating a sample for the presence of a target analyte further includes imaging the labelling composition contacted sample using fluorescence microscopy. Fluorescence microscopy imaging can be used to identify a polymeric dye conjugate-target analyte binding complex in the contacted sample to evaluate whether the target analyte is present. Microscopy methods of interest that find use in the subject methods include laser scanning confocal microscopy.

Also provided are methods of labelled a target molecule. The subject polymeric tandem dyes, find use in a variety of methods of labelling, separation, detection and/or analysis. In some embodiments, the method includes: contacting the target molecule with a polymeric tandem dye to produce a labelled target molecule, wherein the polymeric dye includes: a water soluble light harvesting multichromophore comprising a conjugated segment comprising: a fluorene co-monomer; and a luminescent metal complex covalently linked to the multichromophore in energy-receiving proximity therewith; and a conjugation tag that covalently links to the target molecule.

In some instances of the method, the labelled specific binding member includes a multichromophore according to any one of formulae (X) and (XIX)-(XII) (e.g., as described herein), where one of $G^1$ and $G^2$ is a terminal group and the other of $G^1$ and $G^2$ is the conjugation tag. In some instances, $F^1$ is a fluorene co-monomer.

As used herein the term "conjugation tag" refers to a group that includes a chemoselective functional group (e.g., as described herein) that can covalently link with a compatible functional group of a target molecule, after optional activation and/or deprotection. Any convenient conjugation tags may be utilized in the subject polymeric dyes in order to conjugate the dye to a target molecule of interest. In some embodiments, the conjugation tag includes a terminal functional group selected from an amino, a carboxylic acid or a derivative thereof, a thiol, a hydroxyl, a hydrazine, a hydrazide, a azide, an alkyne and a protein reactive group (e.g. amino-reactive, thiol-reactive, hydroxyl-reactive, imidazolyl-reactive or guanidinyl-reactive).

Any convenient methods and reagent may be adapted for use in the subject labelling methods in order to covalently link the conjugation tag to the target molecule. Methods of interest for labelling a target, include but are not limited to, those methods and reagents described by Hermanson, Bioconjugate Techniques, Third edition, Academic Press, 2013. The contacting step may be performed in an aqueous solution. In some instances, the conjugation tag includes an amino functional group and the target molecule includes an activated ester functional group, such as a NHS ester or sulfo-NHS ester, or vice versa. In certain instances, the conjugation tag includes a maleimide functional group and the target molecule includes a thiol functional group, or vice versa.

Any convenient target molecules may be selected for labelling utilizing the subject methods. Target molecules of interest include, but are not limited to, a nucleic acid, such as an RNA, DNA, PNA, CNA, HNA, LNA or ANA molecule, a protein, such as a fusion protein, a modified protein, such as a phosphorylated, glycosylated, ubiquitinated, SUMOylated, or acetylated protein, or an antibody, a peptide, an aggregated biomolecule, a cell, a small molecule, a vitamin and a drug molecule. As used herein, the term "a target protein" refers to all members of the target family, and fragments thereof. The target protein may be any protein of interest, such as a therapeutic or diagnostic target, including but not limited to: hormones, growth factors, receptors, enzymes, cytokines, osteoinductive factors, colony stimulating factors and immunoglobulins. The term "target protein" is intended to include recombinant and synthetic molecules, which can be prepared using any convenient recombinant expression methods or using any convenient synthetic methods, or purchased commercially. In some embodiments, the target molecule is a specific binding member (e.g., as described herein). In certain instances, the specific binding member is an antibody. In some instances, the specific binding member is an antibody fragment or binding derivative thereof. In some case, the antibody fragment or binding derivative thereof is selected from the group consisting of a Fab fragment, a $F(ab')_2$ fragment, a scFv, a diabody and a triabody.

In some cases, the method includes a separating step where the labelled target molecule is separated from the reaction mixture, e.g., excess reagents or unlabeled target. A variety of methods may be utilized to separate a target from a sample, e.g., via immobilization on a support, precipitation, chromatography, and the like.

In some instances, the method further includes detecting and/or analyzing the labelled target molecule. In some instances, the method further includes fluorescently detecting the labelled target molecule. Any convenient methods may be utilized to detect and/or analyze the labelled target molecule in conjunction with the subject methods and compositions. Methods of analyzing a target of interest that find use in the subject methods, include but are not limited to, flow cytometry, fluorescence microscopy, in-situ hybridization, enzyme-linked immunosorbent assays (ELISAs), western blot analysis, magnetic cell separation assays and fluorochrome purification chromatography. Detection methods of interest include but are not limited to fluorescence spectroscopy, fluorescence microscopy, nucleic acid sequencing, fluorescence in-situ hybridization (FISH), protein mass spectroscopy, flow cytometry, and the like.

Detection may be achieved directly via the polymeric tandem dye, or indirectly by a secondary detection system. The latter may be based on any one or a combination of several different principles including, but not limited to, antibody labelled anti-species antibody and other forms of immunological or non-immunological bridging and signal amplification systems (e.g., biotin-streptavidin technology, protein-A and protein-G mediated technology, or nucleic acid probe/anti-nucleic acid probes, and the like). Suitable reporter molecules may be those known in the field of immunocytochemistry, molecular biology, light, fluorescence, and electron microscopy, cell immunophenotyping, cell sorting, flow cytometry, cell visualization, detection, enumeration, and/or signal output quantification. More than one antibody of specific and/or non-specific nature might be labelled and used simultaneously or sequentially to enhance target detection, identification, and/or analysis.

Systems

Aspects of the invention further include systems for use in practicing the subject methods and compositions. A sample analysis system can include sample field of view or a flow channel loaded with a sample and a labelled specific binding member. In some embodiments, the system is a flow cytometric system including: a flow cytometer including a flow path; a composition in the flow path, wherein the composition includes: a sample; and a labelled specific binding member (e.g., as described herein).

In some embodiments, the system for analyzing a sample is a fluorescence microscopy system, including: a fluorescence microscope comprising a sample field of view; and a composition disposed in the sample field of view, wherein the composition comprises a sample; and a labelled specific binding member (e.g., as described herein).

In some instances of the systems, the labelled specific binding member includes: a water soluble light harvesting multichromophore (e.g., as described herein) comprising a conjugated segment including: a fused 6-5-6 tricyclic co-monomer (e.g., a fluorene co-monomer, as described herein); and a luminescent metal complex covalently linked to the multichromophore in energy-receiving proximity therewith (e.g., as described herein); and a specific binding member covalently linked to the multichromophore.

In some instances of the subject systems, the labelled specific binding member, the multichromophore is described by any one of formulae (X) and (XIX)-(XII) (e.g., as described herein), wherein: $G^1$ and $G^2$ are each independently selected from the group consisting of a terminal group, a π conjugated segment, a linker and a linked specific binding member, wherein at least one of $G^1$ and $G^2$ is a linked specific binding member. In some instances, $F^1$ is a fluorene co-monomer.

In certain embodiments of the systems, the composition further includes a second specific binding member that is support bound and specifically binds the target analyte. In some cases, the support includes a magnetic particle. As such, in certain instances, the system may also include a controllable external paramagnetic field configured for application to an assay region of the flow channel.

The sample may include a cell. In some instances, the sample is a cell-containing biological sample. In some instances, the sample includes a labelled specific binding member specifically bound to a target cell. In certain instances, the target analyte that is specifically bound by the specific binding member is a cell surface marker of the cell. In certain cases, the cell surface marker is selected from the group consisting of a cell receptor and a cell surface antigen.

In certain aspects, the system may also include a light source configured to direct light to an assay region of the flow channel or sample field of view. The system may include a detector configured to receive a signal from an assay region of the flow channel or a sample field of view, wherein the signal is provided by the fluorescent composition. Optionally further, the sample analysis system may include one or more additional detectors and/or light sources for the detection of one or more additional signals.

In certain aspects, the system may further include computer-based systems configured to detect the presence of the fluorescent signal. A "computer-based system" refers to the hardware means, software means, and data storage means used to analyze the information of the present invention. The minimum hardware of the computer-based systems of the present invention includes a central processing unit (CPU), input means, output means, and data storage means. A skilled artisan can readily appreciate that any one of the currently available computer-based system are suitable for use in the subject systems. The data storage means may include any manufacture including a recording of the present information as described above, or a memory access means that can access such a manufacture.

To "record" data, programming or other information on a computer readable medium refers to a process for storing information, using any such methods as known in the art. Any convenient data storage structure may be chosen, based on the means used to access the stored information. A variety of data processor programs and formats can be used for storage, e.g., word processing text file, database format, etc.

A "processor" references any hardware and/or software combination that will perform the functions required of it. For example, any processor herein may be a programmable digital microprocessor such as available in the form of an electronic controller, mainframe, server or personal computer (desktop or portable). Where the processor is programmable, suitable programming can be communicated from a remote location to the processor, or previously saved in a computer program product (such as a portable or fixed computer readable storage medium, whether magnetic, optical or solid state device based). For example, a magnetic medium or optical disk may carry the programming, and can be read by a suitable reader communicating with each processor at its corresponding station.

In addition to the sensor device and signal processing module, e.g., as described above, systems of the invention may include a number of additional components, such as data output devices, e.g., monitors and/or speakers, data input devices, e.g., interface ports, keyboards, etc., fluid handling components, power sources, etc.

In certain aspects, the system includes a flow cytometer. Flow cytometers of interest include, but are not limited to, those devices described in U.S. Pat. Nos. 4,704,891; 4,727,029; 4,745,285; 4,867,908; 5,342,790; 5,620,842; 5,627,037; 5,701,012; 5,895,922; and 6,287,791; the disclosures of which are herein incorporated by reference.

Other systems may find use in practicing the subject methods. In certain aspects, the system may be a fluorimeter or microscope loaded with a sample having a fluorescent composition of any of the embodiments discussed herein. The fluorimeter or microscope may include a light source configured to direct light to the assay region of the flow channel or sample field of view. The fluorimeter or microscope may also include a detector configured to receive a signal from an assay region of the flow channel or field of view, wherein the signal is provided by the fluorescent composition.

Kits

Aspects of the invention further include kits for use in practicing the subject methods and compositions. The compositions of the invention can be included as reagents in kits either as starting materials or provided for use in, for example, the methodologies described above.

A kit can include a polymeric tandem dye (e.g., as described herein) including a water soluble light harvesting multichromophore including a conjugated segment including: a fused 6-5-6 tricyclic co-monomer; and a luminescent metal complex covalently linked to the multichromophore in energy-receiving proximity therewith (e.g., as described herein); and one or more components selected from the group consisting of a polymeric tandem dye, a fluorophore, a specific binding member, a specific binding member conjugate, a support bound specific binding member, a cell, a support, a biocompatible aqueous elution buffer, and instructions for use. In some embodiments of the kit, the multichromophore is covalently linked to a specific binding member. In some instances, the specific binding member is an antibody. In certain instances, the specific binding member is an antibody fragment or binding derivative thereof. In certain cases, the antibody fragment or binding derivative thereof is selected from the group consisting of a Fab fragment, a F(ab')2 fragment, a scFv, a diabody and a triabody.

In certain embodiments, the kit finds use in evaluating a sample for the presence of a target analyte, such as an intracellular target. As such, in some instances, the kit includes one or more components suitable for lysing cells. The one or more additional components of the kit may be provided in separate containers (e.g., separate tubes, bottles, or wells in a multi-well strip or plate).

In certain aspects, the kit further includes reagents for performing a flow cytometric assay. Reagents of interest include, but are not limited to, buffers for reconstitution and dilution, buffers for contacting a cell sample the multichromophore, wash buffers, control cells, control beads, fluorescent beads for flow cytometer calibration and combinations thereof. The kit may also include one or more cell fixing reagents such as paraformaldehyde, glutaraldehyde, methanol, acetone, formalin, or any combinations or buffers thereof. Further, the kit may include a cell permeabilizing reagent, such as methanol, acetone or a detergent (e.g., triton, NP-40, saponin, tween 20, digitonin, leucoperm, or any combinations or buffers thereof. Other protein transport inhibitors, cell fixing reagents and cell permeabilizing reagents familiar to the skilled artisan are within the scope of the subject kits.

The compositions of the kit may be provided in a liquid composition, such as any suitable buffer. Alternatively, the compositions of the kit may be provided in a dry composition (e.g., may be lyophilized), and the kit may optionally include one or more buffers for reconstituting the dry composition. In certain aspects, the kit may include aliquots of the compositions provided in separate containers (e.g., separate tubes, bottles, or wells in a multi-well strip or plate).

In addition, one or more components may be combined into a single container, e.g., a glass or plastic vial, tube or bottle. In certain instances, the kit may further include a container (e.g., such as a box, a bag, an insulated container, a bottle, tube, etc.) in which all of the components (and their separate containers) are present. The kit may further include packaging that is separate from or attached to the kit container and upon which is printed information about the kit, the components of the and/or instructions for use of the kit.

In addition to the above components, the subject kits may further include instructions for practicing the subject methods. These instructions may be present in the subject kits in a variety of forms, one or more of which may be present in the kit. One form in which these instructions may be present is as printed information on a suitable medium or substrate, e.g., a piece or pieces of paper on which the information is printed, in the packaging of the kit, in a package insert, etc. Yet another means would be a computer readable medium, e.g., diskette, CD, DVD, portable flash drive, etc., on which the information has been recorded. Yet another means that may be present is a website address which may be used via the Internet to access the information at a removed site. Any convenient means may be present in the kits.

Utility

The polymeric tandem dyes, compositions, methods and systems as described herein may find use in a variety of applications, including diagnostic and research applications, in which the labelling detection and/or analysis of a target of interest is desirable. Such applications include methodologies such as cytometry, microscopy, immunoassays (e.g. competitive or non-competitive), assessment of a free analyte, assessment of receptor bound ligand, and so forth. The compositions, system and methods described herein may be useful in analysis of any of a number of samples, including but not limited to, biological fluids, cell culture samples, and tissue samples. In certain aspects, the compositions, system and methods described herein may find use in methods where analytes are detected in a sample, if present, using fluorescent labels, such as in fluorescent activated cell sorting or analysis, immunoassays, immunostaining, and the like. In certain instances, the compositions and methods find use in applications where the evaluation of a sample for the presence of a target analyte is of interest.

In some cases, the methods and compositions find use in any assay format where the detection and/or analysis of a target from a sample is of interest, including but not limited to, flow cytometry, fluorescence microscopy, in-situ hybridization, enzyme-linked immunosorbent assays (ELISAs), western blot analysis, magnetic cell separation assays and fluorochrome purification chromatography. In certain instances, the methods and compositions find use in any application where the fluorescent labelling of a target molecule is of interest. The subject compositions may be adapted for use in any convenient applications where pairs of specific binding members find use, such as biotin-streptavidin and hapten-anti-hapten antibody.

EXAMPLES

Example 1: Synthesis of Photostable Polymeric Tandem Dye MC-Ru

Figure 2:
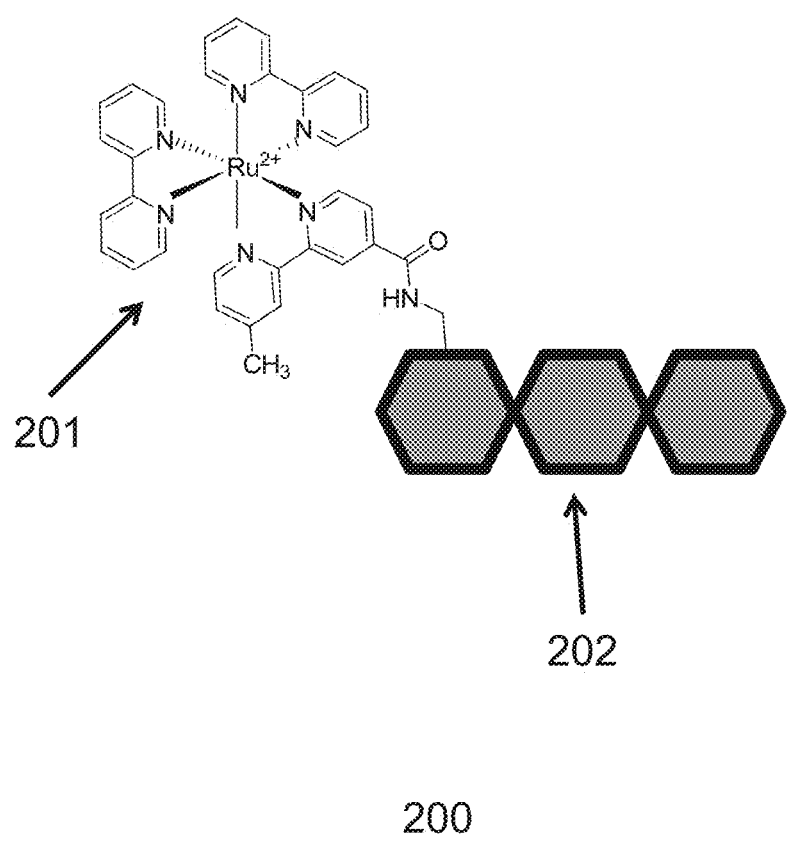
FIG. 2 illustrates a schematic of an exemplary photostable polymeric tandem dye (MC-Ru) (200), which features a ruthenium bipyridine derivative metal complex (Ru(bpy)) (201) appended to an exemplary light harvesting multichromophore (MC core) (202).

A polymeric tandem dye (MC-Ru) that features a ruthenium bipyridine analog conjugated to a multichromophore core polymer (FIG. 2) was prepared according to the following exemplary procedure.

Materials:

1. Multichromophore including fluorene linking co-monomer having sidechain amino functional groups (—NH$_2$) (MC core):

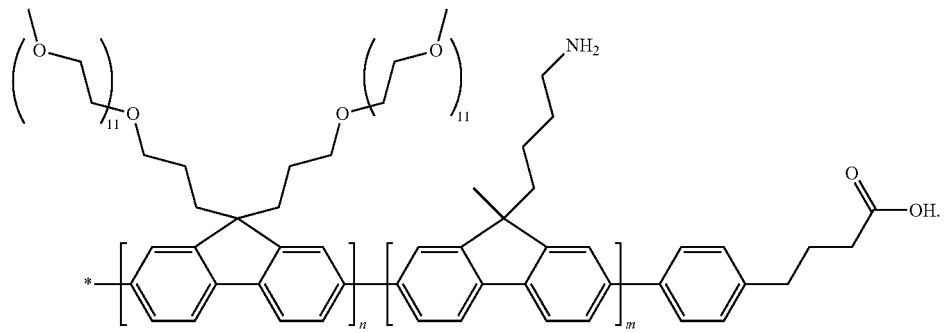

2. Ru(bpy)-NHS; bis(2,2-bipyridine)-4'-methyl-4-carboxy-bipyridine-ruthenium N-succinimidyl ester-bis(hexafluorophosphate) (Sigma, Cat:96631; MW: 1014.66 g mol-1).

Procedure:

1. Make an 80 mg·mL$^{-1}$ stock solution of MC core in 20% (v/v) EtOH in DMSO. By dissolving 25.9 mg of MC CORE in 323 µL of the EtOH/DMSO solution. Assuming a MW of 60 kDa for MC CORE, 25. 9 mg is 0.43 µmols. 80 mg/mL MC CORE=1.33 mM 2. Dissolve 5 mg (4.9 µmols) of Ru(bpy)-NHS in 500 µL of DMSO to make a 9.8 mM solution.

3. In a 1.5 mL Eppendorf tube, place:
   a. 37.7 µL of 1.33 mM MC CORE
   b. 862 µL of PBS, pH=8
   C. 100 µL of 9.8 mM Ru(bpy)-NHS, added in 4×25 µL portions with mixing in between each portion.

4. Mix the solution, which contained ca. 50 µM MC CORE and 1 mM Ru(bpy)-NHS, in the dark at RT using a rotating Eppendorf tube rack.

5. After 4 hours, remove unreacted Ru(bpy) using a Zeba spin column with a 7 kDa MW cut-off, according to manufacturer's specifications.

Example 2: Properties of Photostable Polymeric Tandem Dye MC-Ru

Figure 3:
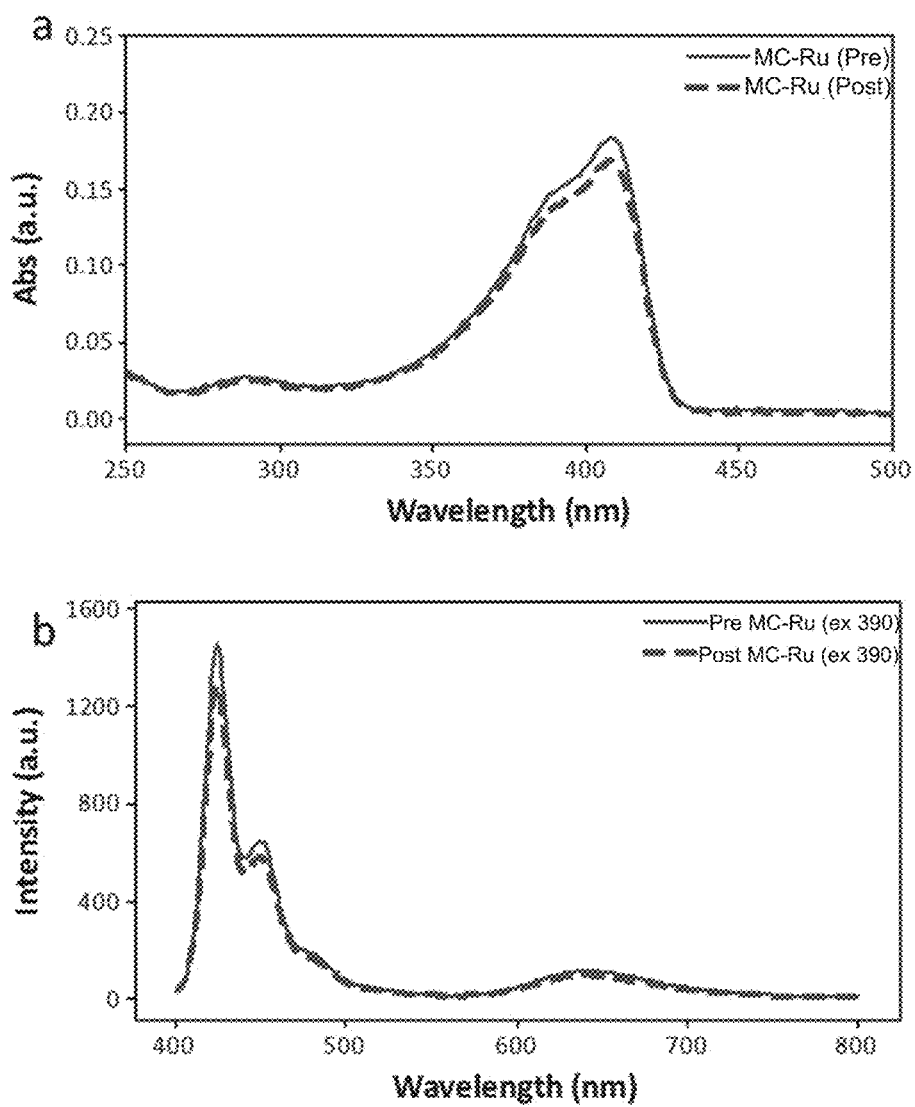
FIG. 3, panels a-b illustrate absorbance (panel a) and emission (panel b) spectra of a 90 nM solution of MC-Ru in PBS buffer before (pre, solid line) and after (post, dashed line) continuous exposure to light ($\lambda$ex=390 nm).

To characterize the photophysical properties of MC-Ru, the absorbance and emission spectra of the polymeric tandem dye were obtained, the quantum yield was measured, and an in vitro photostability assay was carried out. The absorbance and emission spectra of MC-Ru were obtained. FIG. 3 shows absorbance (panel a) and emission (panel b) spectra of a 90 nM solution of MC-Ru in PBS (phosphate buffered saline) buffer before (pre, solid line) and after (post, dashed line) continuous exposure to incident excitation light ($\lambda_{ex}$=390 nm). The sample was continuously irradiated with light ($\lambda_{ex}$=450) for 60 min. Excitation and emission slit widths were 1 mm (4 nm) and 0.25 mm (1 nm), respectively. Fluorescence intensity was monitored at $\lambda_{em}$=640 nm. Data are reported as a percentage of normalized intensity (normalized intensity=(I640 nm/Iinitial 640 nm)×100). Emission wavelength scans were acquired before (Pre) and after (Post) the photostability study. The absorbance spectrum of MC-Ru appears analogous to the absorbance spectrum of MC core light harvesting chromophore with the exception of a small band at A $\lambda_{abs}$=288 nm, which is assigned to the π→π* transition of the bipyridine ligands (see FIG. 3, panel a). When the solution of MC-Ru is excited ($\lambda_{ex}$=390 nm), emission bands from both the MC core polymer ($\lambda_{em}$=425 and 450 nm) and the Ru(bpy) complex ($\lambda_{em}$=640 nm) are observed (FIG. 3b).

Figure 4:
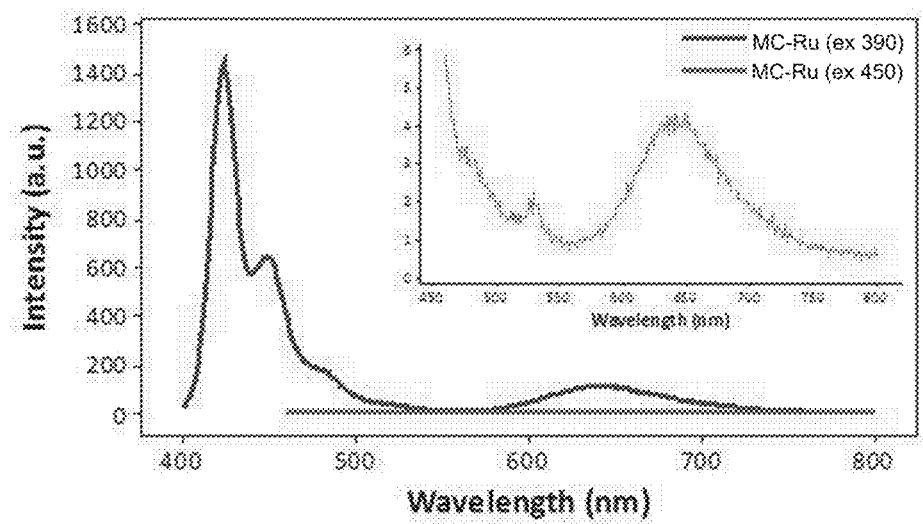
FIG. 4 illustrates emission spectra of MC-Ru in PBS buffer when excited by the multichromophore ($\lambda$ex=390 nm; black line) and the emission spectra of the Ru(bpy) metal complex moiety conjugated to the polymer backbone when it is directly excited ($\lambda$ex=450 nm, grey line.) Inset: Close-up of the emission band observed when the Ru(bpy) metal complex moieties are directly excited with the 450 nm light.

FIG. 4 shows the emission spectrum of MC-Ru in PBS buffer when either the MC Core polymeric multichromophore is excited ($\lambda_{ex}$=390 nm; black line) or the Ru(bpy) metal ligand moiety conjugated to the backbone of the polymeric multichromophore is directly excited ($\lambda_{ex}$=450 nm, grey line). The inset spectra is a close-up of the emission band observed when the Ru(bpy) metal ligand moieties are directly excited with 450 nm light. If the Ru(bpy) metal complex moiety of MC-Ru is directly excited ($\lambda_{ex}$=450), an emission signal ($\lambda_{em}$=640 nm) is observed that is ca. 25-fold less intense than when the metal complex is indirectly excited, e.g., via excitation of the MC light harvesting multichromophore at 390 nm and energy transfer (FIG. 4 inset). The 25-fold improvement in fluorescence emission for MC-Ru at 640 nm demonstrates MC-Ru overcomes the lack of brightness observed in most luminescent metal complexes—a significant limitation which has limited the utility of luminescent metal complexes in fluorescence sensing.

To better understand the photophysics of MC-Ru, the quantum yields of a polymeric multichromophore (MC Core) and MC-Ru polymeric tandem dye were calculated as shown in Table 1. Quantum yields were determined using 4-methylumbelliferone (4-MU) as a reference dye (φ=0.7 at pH 10). The excitation wavelength used for all measurements was 390 nm. MC-Ru and MC Core were found to have quantum yields of 3% and 43%, respectively. The large decrease in the quantum yield of MC-Ru is attributed to the low quantum yield of the Ru(bpy) acceptor dye, which is known to be approximately 6% in aerated buffer (Suzuki, 2009). Yet, because of the large extinction coefficient of the MC core polymer, the brightness of MC-Ru, defined as the product of extinction coefficient (ε) and quantum yield (φ), is comparable to that of fluorescein under similar conditions (Table 2).

TABLE 1

Quantum yields for MC core and MC-Ru.

| Sample | $\varphi^a$ (395-550 nm) | $\varphi^b$ (395-800 nm) |
|---|---|---|
| MC core | 0.43(1) | 0.44(1) |
| MC-Ru | 0.030(1) | 0.038(2) |

$^a$Fluorescence emission intensity integrated between 395-550 nm.
$^b$Fluorescence emission intensity integrated between 395-550 nm.
Note regarding parentheses in table: e.g., 0.43(1) refers to 0.43 ± 0.01.

TABLE 2

Brightness comparison of MC core, MC-RU and other fluorescent dyes.

| Fluorophore | Brightness (ε × φ, mM$^{-1}$ cm$^{-1}$) |
|---|---|
| MC core | 880 |
| MC-Ru | 76 |
| Ru(bpy)$_3^{2+}$ | 0.072 |
| Fluorescein | 69 |

Figure 5:
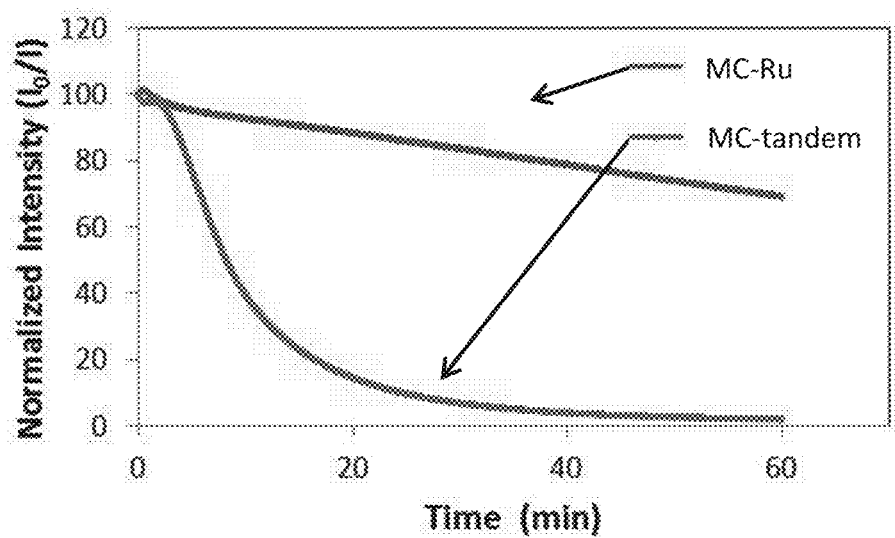
FIG. 5 illustrates the relative photostability of an exemplary photostable polymeric tandem dye (MC-Ru) and an exemplary polymeric light harvesting multichromophore (MC core) that does not include a metal complex.

The photostability of MC-Ru and a MC-tandem polymeric dye (FIG. 5) were compared. The photostability of the dyes was evaluated by continuously irradiating solutions of the dyes and observing the intensity of fluorescence over time. Solutions were exposed to continuous irradiation of light for a period of 60 min. During the exposure the emission intensity of each compound was monitored and values were normalized to initial emission intensity. MC-Ru was relatively photostable under these conditions, losing only about 30% of signal intensity. In contrast, the emission from MC-tandemdropped by 50% in just 8 min and lost >99% of intensity after 60 min. FIG. 5 shows the normalized photostabilities of MC-Ru versus MC-tandem which includes a MC core light harvesting multichromophore and a conjugated organic fluorophore.

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims.

Accordingly, the preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art, and are to be construed as being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the exemplary embodiments shown and described herein. Rather, the scope and spirit of present invention is embodied by the following.

What is claimed is:

1. A photostable polymeric tandem dye comprising:
   a water soluble light harvesting multichromophore comprising a block copolymer comprising a conjugated segment comprising a fluorene co-monomer substituted with at least one water solubilizing group (WSG); and
   a luminescent ruthenium complex covalently linked to the multichromophore in energy-receiving proximity therewith.

2. The polymeric tandem dye according to claim 1, wherein the luminescent metal complex is configured for excitation by the multichromophore and to produce a luminescent metal complex emission that maintains at least 50% intensity for 30 minutes or more during exposure to incident excitation light.

3. The polymeric tandem dye according to claim 2, wherein the luminescent metal complex emission has a quantum yield of 0.03 or more and a brightness of 50 mM$^{-1}$cm$^{-1}$ or more.

4. The polymeric tandem dye according to claim 1, wherein the fluorene co-monomer is substituted with at least one non-ionic WSG group comprising polyethylene glycol and capable of imparting solubility in water in excess of 10 mg/mL.

5. The polymeric tandem dye according to claim 1, wherein the polymeric tandem dye is described by formula (X):

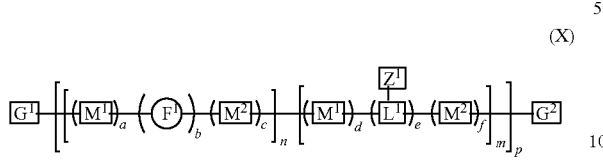

(X)

wherein:
$F^1$ is the fluorene co-monomer;
each $M^1$ and $M^2$ are independently a co-monomer;
$L^1$ is a linking co-monomer substituted with a linked luminescent ruthenium complex $Z^1$;
e is 1;
a, b, c, d and f are each independently 0 or 1, wherein $a+b+c+d+f \geq 1$;
n is 0 or an integer from 1 to 10,000;
m is 0 or an integer from 1 to 10,000;
p is an integer from 1 to 100,000;
$G^1$ and $G^2$ are each independently selected from a terminal group, a π conjugated segment, a linker and a linked specific binding member; and
there is no delocalization of pi electrons between $L^1$ and $Z^1$.

6. The polymeric tandem dye according to claim 5, wherein:
b is 1;
$a+c \geq 1$;
$d+f \geq 1$;
n is an integer from 1 to 10,000; and
m is an integer from 1 to 10,000.

7. The polymeric tandem dye according to claim 5, wherein the polymeric tandem dye is described by formula (XX):

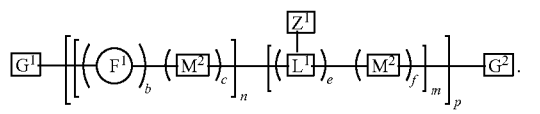

(XX)

8. The polymeric tandem dye according to claim 7, wherein:
b is 1;
c is 0 or 1;
e and f are each 1;
$G^1$ is a terminal group; and
$G^2$ is a terminal group, a linker or a linked specific binding member.

9. The polymeric tandem dye according to claim 5, wherein the polymeric tandem dye is described by formula (XIX):

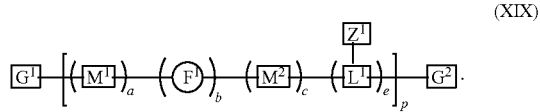

(XIX)

10. The polymeric tandem dye according to claim 5, wherein:
$G^1$ is a terminal group; and
$G^2$ is a terminal group, a linker or a linked specific binding member.

11. The polymeric tandem dye according to claim 5, wherein the $M^1$ and $M^2$ co-monomers are independently an optionally substituted aryl or heteroaryl co-monomer.

12. The polymeric tandem dye according to claim 5, wherein the $M^1$ and $M^2$ co-monomers are independently a substituted or unsubstituted co-monomer selected from 2,1,3-benzothiadiazole, 2,1,3-benzoxadiazole, benzoselenadiazole, benzotellurodiazole, naphthoselenadiazole, 4,7-di(thien-2-yl)-2,1,3-benzothiadiazole, squaraine dyes, quinoxalines, perylene, perylene diimides, diketopyrrolopyrrole, thienopyrazine low bandgap commercial dyes, olefin, cyano-substituted olefin, phenyl, biphenyl, and pyridyl.

13. The polymeric tandem dye according to claim 12, wherein the $M^1$ and $M^2$ co-monomers are independently selected from the group consisting of substituted or unsubstituted 1,4-phenyl, a substituted or unsubstituted 1,3-phenyl, a substituted or unsubstituted 4,4'-biphenyl, a substituted or unsubstituted 2,5-pyridyl, and a substituted or unsubstituted 2,6-pyridyl.

14. The polymeric tandem dye according to claim 13, wherein the $M^1$ and $M^2$ co-monomers are independently selected from the group consisting of the following:

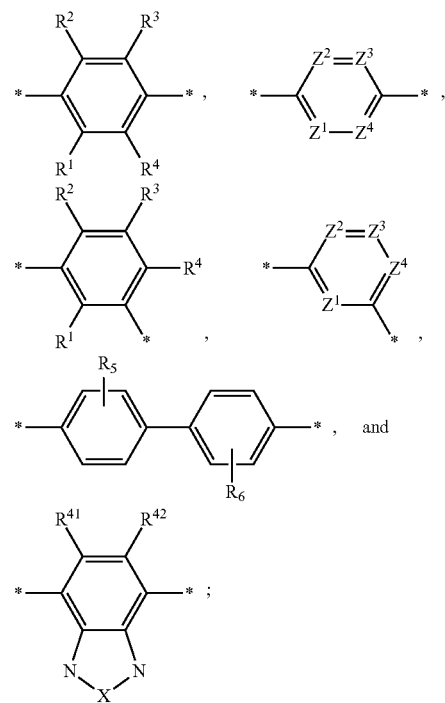

wherein:
$Z^1-Z^4$ are each independently CR or N, wherein at least one $Z^1$-$Z^4$ is N;
each R and $R^1$-$R^6$ are independently selected from hydrogen, halogen, WSG, cyano, alkoxy, substituted alkoxy, alkyl and substituted alkyl;
X is O or S;
$R^{41}$ and $R^{42}$ are each independently selected from H, halogen, WSG, alkyl, substituted alkyl, alkoxy and substituted alkoxy; and wherein * denotes site for covalent attachment to the backbone of the conjugated segment.

15. The polymeric tandem dye according to claim 5, wherein $F^1$ is described by the structure:

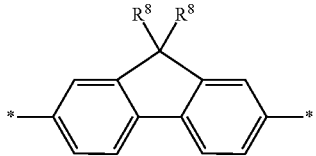

wherein:
each $R^8$ is a substituted alkyl comprising a water soluble group or a substituted aralkyl comprising a water soluble group; wherein * denotes site for covalent attachment to the backbone of the conjugated segment.

16. The polymeric tandem dye according to claim 5, wherein $L^1$ is a fluorene co-monomer.

17. The polymeric tandem dye according to claim 5, wherein $L^1$ is described by the structure:

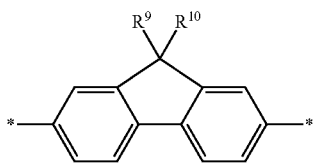

wherein:
$R^9$ is substituted alkyl comprising a water soluble group;
$R^{10}$ is $L^2$-$Z^2$ wherein $L^2$ is a linker and $Z^2$ is the linked luminescent ruthenium complex.

18. The polymeric tandem dye according to claim 1, wherein the luminescent ruthenium complex is a substituted tri(bipyridine)ruthenium complex.

19. The polymeric tandem dye according to claim 5, wherein the luminescent ruthenium complex comprises a substituted multidentate metal chelating ligand of the structure:

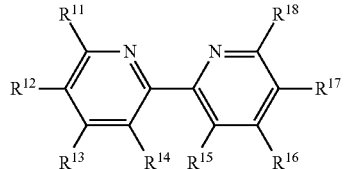

wherein $R^{11}$ to $R^{18}$ are each independently selected from H, alkyl, substituted alkyl, heteroaryl, substituted heteroaryl, aryl, substituted aryl and linker, wherein at least one of $R^{11}$ to $R^{18}$ is covalently linked to the linking co-monomer.

20. The polymeric tandem dye according to claim 19, wherein the substituted multidentate metal chelating ligand is of the structure:

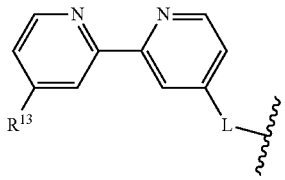

wherein
$R^{13}$ is H, alkyl or substituted alkyl; and
L is a linker that is covalently linked to the linking co-monomer.

21. The polymeric tandem dye according to claim 5, wherein the linking co-monomer comprises 5% to 50% by molarity of the multichromophore.

* * * * *